United States Patent [19]

Oya et al.

[11] Patent Number: 4,499,102

[45] Date of Patent: Feb. 12, 1985

[54] THIAZOLIDINE AND PYRROLIDINE COMPOUNDS AND PHARMACEUTICAL COMPOSITIONS CONTAINING THEM

[75] Inventors: Masayuki Oya, Ibaraki; Tadashi Iso, Sakai, both of Japan

[73] Assignee: Santen Pharmaceutical Co., Ltd., Osaka, Japan

[21] Appl. No.: 329,296

[22] Filed: Dec. 10, 1981

Related U.S. Application Data

[63] Continuation-in-part of Ser. No. 165,561, Jul. 3, 1980, abandoned.

[30] Foreign Application Priority Data

Dec. 13, 1979 [JP] Japan ............................... 54-161977
Dec. 12, 1980 [CA] Canada .................................. 366732
Dec. 12, 1980 [EP] European Pat. Off. ......... 80107869.2
Dec. 24, 1980 [JP] Japan ............................... 55-183379

[51] Int. Cl.³ ................. A61K 31/40; A61K 31/425; C07D 207/16; C07D 277/06
[52] U.S. Cl. .................................... 514/365; 544/131; 544/133; 546/256; 546/280; 548/200; 548/201; 548/533; 548/536
[58] Field of Search .............. 548/200, 201, 533, 536; 546/256, 280; 424/270, 263, 250, 274; 544/133, 131

[56] References Cited

U.S. PATENT DOCUMENTS

| | | | |
|---|---|---|---|
| 4,052,511 | 2/1976 | Cushman et al. | 424/274 |
| 4,192,878 | 3/1980 | Ondetti | 548/201 |
| 4,283,407 | 8/1981 | Malen et al. | 548/200 |
| 4,308,392 | 12/1981 | Petrillo et al. | 548/201 |
| 4,311,705 | 1/1982 | Ondetti et al. | 548/533 |
| 4,347,371 | 8/1982 | Iwao et al. | 548/536 |
| 4,371,699 | 2/1983 | Ohashi et al. | 548/200 |

FOREIGN PATENT DOCUMENTS

2098215 11/1982 United Kingdom ............... 548/200

OTHER PUBLICATIONS

Arimara et al., Chemical Abstracts, vol. 92, Abstract No. 215433d, (1980).
Yoshitomi, P. I., Chem. Abstracts, vol. 90, Abstract No. 204081v, (1979).
Bentley et al., J. Chem. Soc., London, 1949, pp. 2351-2357, (1949).

*Primary Examiner*—Alton D. Rollins
*Attorney, Agent, or Firm*—Frishauf, Holtz, Goodman & Woodward

[57] ABSTRACT

Thiazolidine and pyrrolidine compounds which have the general formula

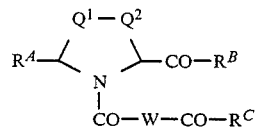

and salts thereof for preventing or relieving diabetic complications and for reducing blood pressure, the processes for their preparation, and the compositions comprising them and pharmaceutically acceptable excipient(s).

17 Claims, No Drawings

THIAZOLIDINE AND PYRROLIDINE COMPOUNDS AND PHARMACEUTICAL COMPOSITIONS CONTAINING THEM

This is a continuation-in-part of application Ser. No. 165,561, filed July 3, 1980, abandoned.

BACKGROUND OF INVENTION

This invention relates to thiazolidine and pyrrolidine compounds of the general formula

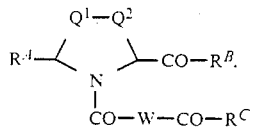

wherein $Q^1$ and $Q^2$ each is methylene or sulfur, but $Q^1$ and $Q^2$ are not sulfur at the same time;
$R^A$ is $R^a$ or $R^b$;
$R^B$ and $R^C$ each is $R^c$;
W is

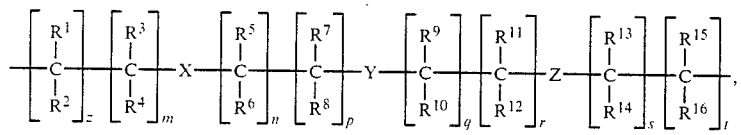

wherein X, Y and Z each is single bond,

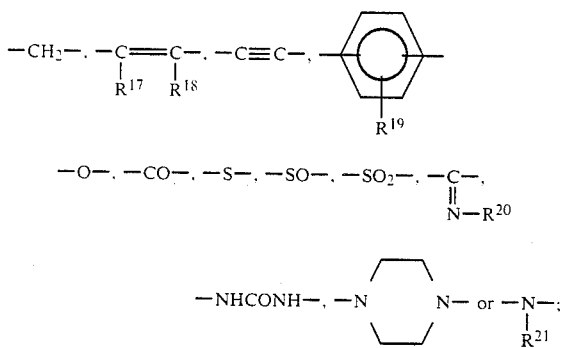

$l$, m, n, p, q, r, s and t each is 0, 1, 2 or 3;
$R^1$, $R^2$, $R^3$, ..., $R^{20}$ and $R^{21}$ each is $R^d$;
$R^A$ is $R^b$ when W is

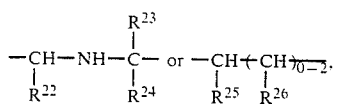

wherein $R^{22}$, $R^{23}$, $R^{24}$, $R^{25}$ and $R^{26}$ each is $R^d$;
$R^a$ is selected from the group consisting of (i) hydrogen, lower alkyl and lower alkenyl, and (ii) lower alkyl and lower alkenyl substituted by at least one substituent selected from the group consisting of lower alkyl, lower alkenyl, hydroxy, lower alkoxy, halogenolower alkoxy, acyloxy, halogen, nitro, cyano, amino, lower alkylamino, dialkylamino, acylamino, mercapto, acylmercapto, lower alkylthio, carboxy, lower alkoxycarbonyl, aralkyloxycarbonyl, aryloxycarbonyl, sulfamoyl, lower alkylaminosulfonyl and lower alkylsulfinyl;

$R^b$ is selected from the group consisting of (a) (i) aralkyl, heteroaralkyl, aralkenyl and heteroaralkenyl, and (ii) aralkyl, heteroalkyl, aralkenyl and heteroaralkenyl substituted by at least one substituent selected from the group consisting of lower alkyl, lower alkenyl, halogeno-lower alkyl, hydroxy, lower alkoxy, halogeno-lower alkoxy, acyloxy, halogen, nitro, cyano, amino, lower alkylamino, dialkylamino, acylamino, mercapto acylmercapto, lower alkylthio, carboxy, lower alkoxycarbonyl, aralkyloxycarbonyl, aryloxycarbonyl, sulfamoyl, lower alkylaminosulfonyl and lower alkylsulfinyl, and (iii) carboxy, lower alkoxycarbonyl, aralkyloxycarbonyl, aryloxycarbonyl and heteroaryloxycarbonyl; (b) (i) phenyl and naphthyl, and (ii) phenyl and naphthyl substituted by at least one substituent selected from the group consisting of lower alkyl, lower alkenyl, halogeno-lower alkyl, hydroxy, lower alkoxy, halogeno-lower alkoxy, aralkyloxy, aryloxy, acyloxy, halogen, nitro, cyano, amino, lower alkylamino, dialkylamino, acylamino, mercapto, acylmercapto, lower alkylthio, carboxy, lower alkoxycarbonyl, aralkyloxycarbonyl, aryloxycarbonyl, sulfamoyl, lower alkylaminosulfonyl and lower alkylsulfinyl; (c) (i) furyl, thienyl and pyridyl, and (ii) furyl, thienyl and pyridyl substituted by at least one substituent selected from the group consisting of lower alkyl, lower alkenyl, halogeno-lower alkyl, hydroxy, lower alkoxy, halogeno-lower alkoxy, aralkyloxy, aryloxy, acyloxy, halogen, nitro, cyano, amino, lower alkylamino, dialkylamino, acylamino, mercapto, acylmercapto, lower alkylthio, carboxy, lower alkoxycarbonyl, aralkyloxycarbonyl, aryloxycarbonyl, sulfamoyl, lower alkylaminosulfonyl and lower alkylsulfinyl;

$R^c$ is selected from the group consisting of (a) (i) hydroxy, lower alkoxy and amino, and (ii) lower alkoxy, and amino substituted by at least one substituent selected from the group consisting of lower alkyl, aralkyl, heteroaralkyl, aralkenyl, heteroaralkenyl, hydroxy, lower alkoxy, aralkyloxy, heteroaralkyloxy, aryloxy, heteroaryloxy, acyloxy, aryl, heteroaryl, substituted aralkyl and substituted aryl wherein the substituent is lower alkyl, lower alkoxy, halogen and amino; (b) (i) aryloxy and heteroaryloxy, and (ii) aryloxy and heteroaryloxy substituted by at least one substituent selected from the group consisting of lower alkyl, hydroxy, lower alkoxy, halogen and amino, and

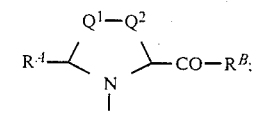

$R^d$ is selected from the group consisting of (a) (i) hydrogen, lower alkyl, lower alkenyl, aralkyl, heteroaralkyl, alkanoyl, arylalkanoyl, heteroarylalkanoyl, hydroxy, carboxy, amino, mercapto and sulfo, and (ii) lower alkyl, lower alkenyl, aralkyl, heteroaralkyl, alkanoyl, arylalkanoyl, heteroarylalkanoyl, hydroxy, carboxy, amino, mercapto and sulfo substituted by at least one substituent selected from the group consisting of lower alkyl, lower alkenyl, lower alkoxy, lower alkanoyl, aryl, heteroaryl, acyloxy, aroyl, hydroxy, carboxy, amino, guanidino, mercapto, acylamino, acylmercapto, lower alkoxycarbonyl, sulfo, halogen, nitro, cyano, sulfamoyl, lower alkylaminosulfonyl, lower alkylthio and lower alkylsulfinyl; (b) (i) phenyl and naphthyl, and (ii) phenyl and naphthyl substituted by at least one substituent selected from the group consisting of lower alkyl, lower alkoxy, lower alkanoyl, acyloxy, hydroxy, carboxy, amino, halogen, nitro, cyano, acylamino, mercapto, acylmercapto, halogeno-lower alkyl, halogeno-lower alkoxy, lower alkylenedioxy, lower alkoxycarbonyl, sulfo, sulfamoyl, lower alkylaminosulfonyl and lower alkylsulfinyl; (c) (i) furyl, thienyl and pyridyl, and (ii) furyl, thienyl and pyridyl substituted by at least one substituent selected from the group consisting of lower alkyl, lower alkoxy, lower alkanoyl, acyloxy, hydroxy, carboxy, amino, halogen, nitro, cyano, acylamino, mercapto, acylmercapto, halogeno-lower alkyl, halogeno-lower alkoxy, lower alkylenedioxy, lower alkoxycarbonyl, sulfo, sulfamoyl, lower alkylaminosulfonyl and lower alkylsulfinyl;

and salts thereof which are useful as agents for therapy or prophylaxis of the diabetic complication because they inhibit strongly aldose reductase, and as antihypertensive agents because they inhibit angiotensin I-converting enzyme.

The compounds [I] of this invention can be prepared by following process.

(i) A compound of the formula [I] is yielded by the reaction of a compound of the formula [II]

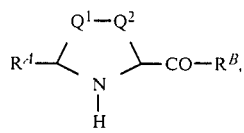  [II]

wherein $R^d$ and $R^B$ may be protected by any suitable groups (e.g., lower alkyl, acyl, aralkyl, aralkyloxy, etc.) when $R^d$ and $R^B$ include reactive groups (e.g., amino, hydroxy, mercapto, hydroxyamino, etc.), with the reactive derivative of carboxylic acid of the formula [III] (e.g., acyl halide, acid anhydride, mixed anhydride, active ester, lactone, etc.) by general methods used in peptide syntheses or amide formation reactions

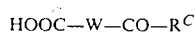  [III], wherein W and $R^C$ may be protected by any suitable groups (e.g., lower alkyl, acyl, aralkyl, aralkyloxy, etc.) when W and $R^C$ include reactive groups (e.g., amino, hydroxy, mercapto, hydroxyamino, etc.), followed by removal of protective groups by well-known methods (e.g., hydrolysis, hydrogenolysis, ammonolysis, alcoholysis, etc.).

This procedures of deprotection can be applied in the following methods.

(ii) A compound of the formula [I] is yielded by the reaction of a compound of the formula [II] with the reactive derivative of carboxylic acid of [IV] (e.g., above-mentioned)

  [IV].

wherein $W^1$ is

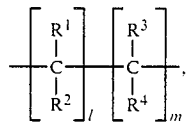

and may be protected such as (i) above, L is a leaving group (e.g., halogen, alkylsulfonyl, arylsulfonyl, etc.), by the same methods as described in (i) above to produce a compound of the formula [V]

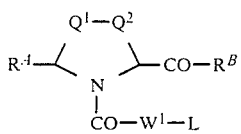  [V]

and then reaction of a compound of the formula [V] with a compound of the formula [VI]

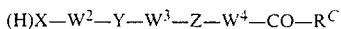  [VI].

wherein $W^2$ is

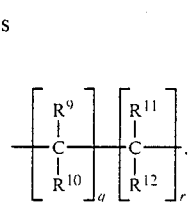

$W^3$ is

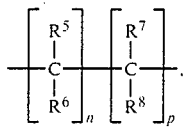

$W^4$ is

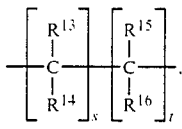

and $W^2$, $W^3$, $W^4$, X, Y, Z and $R^C$ may be protected such as (i) above, in the presence of proper alkaline and/or organic bases, if necessary, by known methods.

(iii) A compound of the formula [I] is yielded by the reaction of a compound of the formula [II] with the reactive derivative of carboxylic acid of the formula [VII] (e.g., metioned in (i) above)

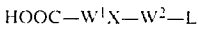  [VII]

and then with a compound of the formula [VIII]

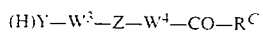

(H)Y—W³—Z—W⁴—CO—R^C    [VIII]

by the same method as (ii) above.

(iv) A compound of the formula [I] is yielded by the reaction of a compound of the formula [II] with the reactive derivative of carboxylic acid of the formula [IX] (e.g., mentioned in (i) above

HOOC—W¹—X—W²—Y—W³—L    [IX].

and then with a compound of the formula [X]

(H)Z—W⁴—CO—R^C    [X]

by the same method as (ii) above.

(v) A compound of the formula [I] is yielded by the reaction of a compound of the formula [II] with the structure derivative of carboxylic acid [XI] (e.g., acyl halide, acid anhydride, mixed anhydride, active ester, lactone, thiolactone, etc.)

HOOC—W¹—X(H)    [XI].

and then with a compound of the formula [XII]

L—W²—Y—W³—Z—W⁴—CO—R^C    [XII]

by the same method as (ii) above.

(vi) A compound of the formula [I] is yielded by the reaction of a compound of the formula [II] with the reactive derivative of carboxylic acid of the formula [XIII] (e.g., mentioned in (v) above)

HOOC—W¹—X—W²—Y(H)    [XIII].

and then with a compound of the formula [XIV]

L—W³—Z—W⁴—CO—R^C    [XIV]

by the same method as (ii) above.

(vii) A compound of the formula [I] is yielded by the reaction of a compound of the formula [II] with the reactive derivative of carboxylic acid of the formula [XV] (e.g., mentioned in (v) above)

HOOC—W¹—X—W²—Y—W³—Z(H)    [XV], and then with a compound of the formula [XVI]

L—W⁴—CO—R^C    [XVI]

by the same method as (ii) above.

(viii) A compound of the formula [I] is also yielded by converting a compound of the formula [I] prepared by any method above-mentioned by well-known methods (e.g., oxidation, formation of oxime, hydrazone and semicarbazone, addition to double bond, etc.)

The compounds [I] of this invention are effective on preventing or relieving diabetic complications.

In diabetic patients, high levels of hexoses (e.g., glucose, galactose, etc.) in blood lead to the accumulation of sugar alcohols (e.g., sorbitol, galactitol, etc.) in tissues. It is known that this accumulation causes the swelling of cells to induce complications of diabetic cataract, diabetic retinopathy, diabetic nephropathy, diabetic neuropathy, etc. [R. Quan-Ma et al., Biochem. Biophys. Res. Comm., 22, 492 (1966)]. For example, R. Gitzelman et al. have presented that cataract is caused by the accumulation of sugar alcohols [Exptl. Eye. Res., 6, 1 (1967)]. A report of Kinoshita et al. has demonstrated that aldose reductase which reduced aldose to the corresponding sugar alcohols was involved in the initiation of these diabetic complications and that effective inhibitors of aldose reductase were useful [Jpn. J. Ophthalmol., 20, 339 (1976)]. On the basis of the above information, aldose reductase inhibition of the compounds [I] of this invention was tested. The results of the examinations demonstrated that these compounds have potent inhibitory activities on aldose reductase, and therefore they are useful as drugs for therapy or prophylaxis of the diabetic complications.

On the other hand, it has been known that a kind of the derivatives of thiazolidine- or pyrrolidinecarboxylic acid have potent inhibitory activity to angiotensin I-converting enzyme, but thiazolidine and pyrrolidine compounds of this invention are novel compounds, and have more potent inhibitory activities to angiotensin I-converting enzyme. Furthermore, the compounds of this invention are prepared by convenient methods, and are superior to the stability.

Thus, the compounds of this invention are useful as therapeutic or prophylactic agents and antihypertensive agents.

The compound of formula [I] can form the conventional salts to be generally used as medicine such as sodium salt, potassium salt, calcium salt, magnesium salt, alminum salt, ammonium salt, diethylamine salt, triethanolamine, etc.

The compounds of formula [I] have the stereoisomers which are within the limit of this invention, because they have one or more asymmetric carbon atoms.

Typical examples are shown below, although this invention is not limited to these examples.

EXAMPLE 1

(4R)-3-(7-Carboxyheptanoyl)-2-(2-hydroxyphenyl)-4-thiazolidinecarboxylic acid (compound 20)

(4R)-2-(2-Hydroxyphenyl)-4-thiazolidinecarboxylic acid (6.8 g), in N sodium hydroxide (30 ml) and octanedioyl dichloride (6.3 g), were added dropwise to 1M potassium carbonate (60 ml) with stirring under ice-cooling. After the addition, the reaction mixture was stirred for 1 hour at the same temperature and for additional 1 hour at room temperature. The solution was acidified with dilute hydrochloric acid, and extracted with ethyl acetate. The organic layer was washed with saturated sodium chloride solution, dried over anhydrous magnesium sulfate, and evaporated in vacuo. The residual oil*² was purified by silica gel column chromatography to give 7.0 g (61%) of the titled compound: mp 155°–157° C. (dec.) (ethyl acetate); [α]$_D^{27}$ +134.1° (c=0.5, methanol). IR (nujol, cm⁻¹): 3220 (OH), 1710 (COOH), 1620 (CON), 1600 (aromatic), 1415, 1235, 1172, 950, 760. NMR (DMSO-d₆,δ): 0.53–1.73 (8H, m, $\text{-(CH}_2\text{—CH}_2\text{)}_4\text{CH}_2\text{—}$), 1.77–2.57 (4H, m, —CH₂-(CH₂)₄CH₂—), 3.03 (1H, AB$_q$(A part), d, J=11.5, 8.5 Hz, C₅*¹—H$_A$), 3.37 (1H, AB$_q$(B part), d, J=11.5, 6.5 Hz, C₅—H$_B$), 4.60 (1H, dd, J=8.5, 6.5 Hz, C₄—H), 6.28 (1H, s, C₂—H), 6.45–8.07 (4H, m, arom. H), 9.77 (1H, s, C₂—H), 6.45–8.07 (4H, m, arom. H), 9.77 (1H, s, —COOH). TLC: Rf value*³ 0.52.

*² Two spots were observed on the TLC (ethyl acetate-chloroform-acetic acid (10:5:3)), and two products could be separated by silica gel column chromatography. From NMR spectra, the upper and lower spots were identified as the titled compound and (4R,4R')-3,3'-(octanedioyl)bis[2-(2-hydroxyphenyl)-4-thiazolidinecarboxylic acid] (compound 40), respectively.
*3 Silica gel, ethyl acetate-chloroform-acetic acid (10:5:3).

The compounds shown in Table I and III were prepared by the same procedure as described above. The following compounds are also prepared by the same procedure as EXAMPLE 1.

(4R)-3-carboxyacetyl-4-thiazolidinecarboxylic acid
(4R)-3-(3-carboxypropanoyl)-2-phenyl-4-thiazolidinecarboxylic acid
(4R)-3-[3-(2-carboxyethylsulfinyl)propanoyl]-2-(2-hydroxyphenyl)-4-thiazolidinecarboxylic acid
(4R)-3-[[[2-(carboxymethyloxy)ethyl]oxy]acetyl]-2-(2-hydroxyphenyl)-4-thiazolidinecarboxylic acid
(4R)-3-(4-carboxybutanoyl)-2-(3-hydroxyphenyl)-4-thiazolidinecarboxylic acid
(4R)-3-(5-carboxypentanoyl)-2-(4-methylphenyl)-4-thiazolidinecarboxylic acid
(4R)-3-(6-carboxyhexanoyl)-2-(4-chlorophenyl)-4-thiazolidinecarboxylic acid
(4R)-3-(7-carboxyheptanoyl)-2-(4-methoxyphenyl)-4-thiazolidinecarboxylic acid
(4R)-3-(13-carboxytridecanoyl)-2-(2-nitrophenyl)-4-thiazolidinecarboxylic acid
(4R)-3-(7-carboxyheptanoyl)-2-(3-nitrophenyl)-4-thiazolidinecarboxylic acid
(4R)-3-[3-(2-carboxyethylthio)propanoyl]-2-(3-nitrophenyl)-4-thiazolidinecarboxylic acid
(4R)-3-[[[2-(carboxymethyloxy)ethyl]oxy]acetyl]-2-(3-nitrophenyl)-4-thiazolidinecarboxylic acid
(4R)-3-(6-carboxyhexanoyl)-2-(4-nitrophenyl)-4-thiazolidinecarboxylic acid
(4R)-3-(9-carboxynonanoyl)-2-(4-nitrophenyl)-4-thiazolidinecarboxylic acid
(4R)-3-(11-carboxyundecanoyl)-2-(4-nitrophenyl)-4-thiazolidinecarboxylic acid
(4R)-3-[4-(3-carboxypropyloxy)butanoyl]-2-(4-nitrophenyl)-4-thiazolidinecarboxylic acid
(4R)-3-[3-(2-carboxyethylsulfonyl)propanoyl]-2-(4-nitrophenyl)-4-thiazolidinecarboxylic acid
(4R)-3-(9-carboxynonanoyl)-2-(5-chloro-2-hydroxyphenyl)-4-thiazolidinecarboxylic acid
(4R)-3-(11-carboxyundecanoyl)-2-(3,4,5-trimethoxyphenyl)-4-thiazolidinecarboxylic acid
(4R)-3-(13-carboxytridecanoyl)-2-(2-acetoxyphenyl)-4-thiazolidinecarboxylic acid
(4R)-3-(6-carboxyhexanoyl)-2-(2-furyl)-4-thiazolidinecarboxylic acid
(4R)-3-(7-carboxyheptanoyl)-2-(2-thienyl)-4-thiazolidinecarboxylic acid
(4R)-3-(8-carboxyoctanoyl)-2-(3-pyridyl)-4-thiazolidinecarboxylic acid
(4R)-3-(9-carboxynonanoyl)-2-(1-naphthyl)-4-thiazolidinecarboxylic acid
(4R)-3-(5-carboxypentanoyl)-2-(2-hydroxy-4-sulfamoylphenyl)-4-thiazolidinecarboxylic acid
(4R)-3-(6-carboxyhexanoyl)-2-(3-cyanophenyl)-4-thiazolidinecarboxylic acid
(4R)-3-(7-carboxyheptanoyl)-2-(3-difluoromethoxyphenyl)-4-thiazolidinecarboxylic acid
(4R)-3-(8-carboxyoctanoyl)-2-(4-carboxyphenyl)-4-thiazolidinecarboxylic acid
(4R)-3-(9-carboxynonanoyl)-2-(3-methylsulfinylphenyl)-4-thiazolidinecarboxylic acid

EXAMPLE 2

(4R,4'R)-3,3'-(Octanedioyl)bis[2-(2-hydroxyphenyl)-4-thiazolidinecarboxylic acid] (compound 40)

To a stirred solution of (4R)-2-(2-hydroxyphenyl)-4-thiazolidinecarboxylic acid (6.8 g) in 1M potassium carbonate (45 ml), octanedioyl dichloride (3.2 g) was added dropwise under ice-cooling. After the addition, the reaction mixture was stirred for 1 hour at the same temperature and for additional 1 hour at room temperature. The solution was acidified with dilute hydrochloric acid, extracted with ethyl acetate. The organic layer was washed with saturated sodium chloride solution, dried over anhydrous magnesium sulfate, and evaporated in vacuo. The residual oil was purified by silica gel column chromatography to give 7.6 g (86%) of the titled compound: mp 93°–97° C. (dec.); $[\alpha]_D^{27}+123.6°$ (c=0.5, methanol). IR (nujol, cm$^{-1}$): 1720 (COOH), 1620 (CON), 1600 (aromatic), 1230, 1090, 855, 765. NMR (CD$_3$OD) δ: 0.7–1.7 (8H, m, —CH$_2$-(CH$_2$)$_4$-CH$_2$—), 1.8–2.4 (4H, m, —CH$_2$-(CH$_2$)$_4$CH$_2$), 3.25 (4H, d, J=7.5 Hz, C$_5$—H), 4.81 (2H, t, J=7.5 Hz, C$_4$—H), 6.35 (2H, s, C$_2$—H), 6.7–8.0 (8H, m, arom. H). TLC: Rf value* 0.34.
*Silica gel, ethyl acetate-chloroform-acetic acid (10:5:3).

The compounds shown in Table II and III were prepared by the same procedure as described above.

EXAMPLE 3

(4R,4'R)-3,3'-(heptanedioyl)bis[2-(3-cyanophenyl)-4-thiazolidinecarboxylic acid] (compound 36)

To a stirred solution of (4R)-2-(3-cyanophenyl)-4-thiazolidinecarboxylic acid (4.7 g) in 1M sodium carbonate (30 ml), heptanedioyl dichloride (2.1 g) was added dropwise under ice-cooling. The reaction mixture was stirred for 30 minutes at the same temperature, and filtered to give the precipitates. The precipitates were dissolved in hot water (100 ml), and acidified with concentrated hydrochloric acid. The separated crystals were collected by filtration to give 3.5 g (59%) of the titled compound: mp 105°–112° C.; $[\alpha]_D^{25}+115.0°$ (c=1.0, methanol). IR (nujol, cm$^{-1}$): 2270 (CN), 1735 (COOH), 1640 (CON), 1610 (aromatic), 1195, 790 (aromatic). NMR (DMSO-d$_6$) δ: 0.69–1.66 (6H, m, -(CH$_2$—CH$_2$)$_3$CH$_2$—), 1.70–2.50 (4H, m, -(CH$_2$—CH$_2$)$_3$C-H$_2$—), 2.85–3.66 (4H, m, C$_5$—H), 4.69 (1H, dd, J=8.2, 6.0 Hz, C$_4$—H), 5.13 (1H, m, C$_4$—H), 6.16 (1H, s, C$_2$—H), 6.43 (1H, s, C$_2$—H), 7.3–8.3 (8H, m, arom. H). TLC: Rf value* 0.33.
*Silica gel, ethyl acetate-chloroform-acetic acid (10:5:3).

The compounds shown in Table II were prepared by the same procedure as described above. The following compounds are also prepared by the same procedure as EXAMPLE 2 or 3.

(4R,4'R)-3,3'-(propanedioyl)bis(4-thiazolidinecarboxylic acid)
(4R,4'R)-3,3'-(butanedioyl)bis(2-phenyl)-4-thiazolidinecarboxylic acid)
(4R,4'R)-3,3'-(3,3'-sulfinyldipropanoyl)bis[2-(2-hydroxyphenyl)-4-thiazolidinecarboxylic acid]
(4R,4'R)-3,3'-[(ethylenedioxy)diacetyl]bis[2-(2-hydroxyphenyl)-4-thiazolidinecarboxylic acid]
(4R,4'R)-3,3'-[(ethylenedithio)diacetyl]bis[2-(2-hydroxyphenyl)-4-thiazolidinecarboxylic acid]
(4R,4'R)-3,3'-(pentanedioyl)bis[2-(3-hydroxyphenyl)-4-thiazolidinecarboxylic
(4R,4'R)-3,3'-(hexanedioyl)bis[2-(4-methylphenyl)-4-thiazolidinecarboxylic acid]
(4R,4'R)-3,3'-(heptanedioyl)bis[2-(4-chlorophenyl)-4-thiazolidinecarboxylic acid]
(4R,4'R)-3,3'-(octanedioyl)bis[2-(4-methoxyphenyl)-4-thiazolidinecarboxylic acid]

(4R,4'R)-3,3'-(tetradecanedioyl)bis[2-(2-nitrophenyl)-4-thiazolidinecarboxylic acid]
(4R,4'R)-3,3'-(3,3'-thiodipropanoyl)bis[2-(3-nitrophenyl)-4-thiazolidinecarboxylic acid]
(4R,4'R)-3,3'-[(ethylenedioxy)diacetyl]bis[2-(3-nitrophenyl)-4-thiazolidinecarboxylic acid]
(4R,4'R)-3,3'-(heptanedioyl)bis[2-(4-nitrophenyl)-4-thiazolidinecarboxylic acid]
(4R,4'R)-3,3'-(decanedioyl)bis[2-(4-nitrophenyl)-4-thiazolidinecarboxylic acid]
(4R,4'R)-3,3'-(dodecanedioyl)bis[2-(4-nitrophenyl)-4-thiazolidinecarboxylic acid]
(4R,4'R)-3,3'-(4,4'-oxydibutanoyl)bis[2-(4-nitrophenyl)-4-thiazolidinecarboxylic acid]
(4R,4'R)-3,3'-(3,3'-sulfonyldipropanoyl)bis[2-(4-nitrophenyl)-4-thiazolidinecarboxylic acid]
(4R,4'R)-3,3'-(decanedioyl)bis[2-(5-chloro-2-hydroxyphenyl)-4-thiazolidinecarboxylic acid]
(4R,4'R)-3,3'-(dodecanedioyl)bis[2-(3,4,5-trimethoxyphenyl)-4-thiazolidinecarboxylic acid]
(4R,4'R)-3,3'-(tetradecanedioyl)bis[2-(2-acetoxyphenyl)-4-thiazolidinecarboxylic acid]
(4R,4'R)-3,3'-(heptanedioyl)bis[2-(2-furyl)-4-thiazolidinecarboxylic acid]
(4R,4'R)-3,3'-(octanedioyl)bis[2-(2-thienyl)-4-thiazolidinecarboxylic acid]
(4R,4'R)-3,3'-(nonanedioyl)bis[2-(3-pyridyl)-4-thiazolidinecarboxylic acid]
(4R,4'R)-3,3'-(decanedioyl)bis[2-(1-naphthyl)-4-thiazolidinecarboxylic acid]
(4R,4'R)-3,3'-(hexanedioyl)bis[2-(2-hydroxy-5-sulfamoylphenyl)-4-thiazolidinecarboxylic acid]
(4R,4'R)-3,3'-(octanedioyl)bis[2-(3-difluoromethoxyphenyl)-4-thiazolidinecarboxylic acid]
(4R,4'R)-3,3'-(nonanedioyl)bis[2-(4-carboxyphenyl)-4-thiazolidinecarboxylic acid]
(4R,4'R)-3,3'-(decanedioyl)bis[2-(3-methylsulfinylphenyl)-4-thiazolidinecarboxylic acid]

EXAMPLE 4

(4R,4'R)-3,3'-(Heptanedioyl)bis[2-(3-nitrophenyl)-4-thiazolidinecarboxylic acid] (compound 35)

To a stirred solution of (4R)-2-(3-nitrophenyl-4-thiazolidinecarboxylic acid (5.1 g) in 1M sodium carbonate (40 ml), heptanedioyl dichloride (2.1 g) was added dropwise under ice-cooling. The reaction mixture was stirred for 1 hour at the same temperature, and the separated crystals were filtered to give 4.7 g (69%) of the titled compound as disodium salt: mp 111°–113° C. (dec.) (water); $[\alpha]_D^{25}+88.2°$ (c=0.5, methanol). IR (nujol, cm$^{-1}$): 1635 (CON), 1585 (COO$^-$), 1520 and 1355 (NO$_2$), 1095, 730. TLC: Rf value* 0.28.
*Silica gel, ethyl acetate-chloroform-acetic acid (10:5:3).

EXAMPLE 5

(4R)-3-(3-Carboxypropanoyl)-2-(2-hydroxyphenyl)-4-thiazolidinecarboxylic acid (compound 6)

To a stirred solution of (4R)-2-(2-hydroxyphenyl)-4-thiazolidinecarboxylic acid (4.5 g) and triethylamine (4.0 g) in acetone (100 ml), succinic anhydride (2.0 g) was added at room temperature, and stirred for 3 hours at the same temperature. The reaction mixture was concentrated in vacuo, and acidified with dilute hydrochloric acid. The separated oil was extracted with ethyl acetate, and the organic layer was washed with saturated sodium chloride solution, dried over anhydrous magnesium sulfate, and evaporated in vacuo to give 4.9 g (75%) of the titled compound: mp 190°–191° C. (dec.) (ethyl acetate-methanol); $[\alpha]_D^{27}+181.6°$ (c=1.0, methanol). IR (nujol, cm$^{-1}$): 3210 (OH), 1720 (COOH), 1618 (CON), 1602 (aromatic), 1245, 1173, 940, 763. NMR (DMSO-$_6$, δ): 2.0–2.7 (4H, m, —CH$_2$CH$_2$—), 3.03 (1H, AB$_q$(A part), d, J=11.0, 10.0 Hz, C$_5$—H$_A$), 3.36 (1H, AB$_q$(B part), d, J=11.0, 7.0 Hz, C$_5$—H$_B$), 4.61 and 5.07 (1H, dd, J=10.0, 7.0 Hz and m, C$_4$—H), 6.36 (1H, s, C$_2$—H), 6.5–8.0 (4H, arom. H). TLC: Rf value* 0.35.
*Silica gel, ethyl acetate-chloroform-acetic acid (10:5:3).

The compounds shown in Table I and III were prepared by the same procedure as described above. The following compounds are also prepared by the same procedure as EXAMPLE 5.
(4R)-3-(4-carboxy-4-oxobutanoyl)-2-(2-hydroxyphenyl)-4-thiazolidinecarboxylic acid
(4R)-3-(6-carboxy-3,5-dioxohexanoyl)-2-(2-hydroxyphenyl)-4-thiazolidinecarboxylic acid
(4R)-3-[4-carboxy-3-(methoxyimino)butanoyl]-2-(2-hydroxyphenyl)-4-thiazolidinecarboxylic acid.

EXAMPLE 6

(4R)-3-[3-(Methoxycarbonyl)-2-methylpropanoyl]-2-(2-hydroxyphenyl)-4-thiazolidinecarboxylic acid (compound 4)

To a stirred solution of (4R)-2-(2-hydroxyphenyl)-4-thiazolidinecarboxylic acid (11.3 g) in 1M sodium carbonate (80 ml), dl-3-methoxycarbonyl-2-methylpropanoyl chloride (8.2 g) was added dropwise under ice-cooling.

After the addition, the reaction mixture was stirred for 1.5 hours at the same temperature. After the filtration of solution, the filtrate was acidified with dilute hydrochloric acid, and extracted with ethyl acetate. The organic layer was washed with saturated sodium chloride solution, dried over anhydrous magnesium sulfate, and evaporated in vacuo. The residual oil was purified by silica gel column chromatography to give 7.8 g (44%) of the titled compound: $[\alpha]_D^{25}+161.6°$ (c=1.0, methanol). IR (KBr, cm$^{-1}$): 3380 (OH), 1723 (COOH, COOCH$_3$), 1624 (CON), 1235, 1200, 1174, 764.

The compounds shown in Table I and II were prepared by the same procedure as described above.

EXAMPLE 7

(4R)-3-(3-Carboxy-2-methylpropanoyl)-2-(2-hydroxyphenyl)-4-thiazolidinecarboxylic acid (compound 5)

(4R)-3-[3-(Methoxycarbonyl)-2-methylpropanoyl]-2-(2-hydroxyphenyl)-4-thiazolidinecarboxylic acid (compound 4) (7.1 g) was dissolved in 2N sodium hydroxide (40 ml) and stirred for 1 hour at room temperature. The resulting solution was acidified with dilute hydrochloric acid and the separated crystals were filtered to give 5.1 g (75%) of the titled compound: mp 163°–164° C. (dec.) (ethyl acetate); $[\alpha]_D^{25}+174.1°$ (c=1.0, methanol). IR (nujol, cm$^{-1}$): 3330 (OH), 1730 and 1710 (COOH), 1629 (CON), 1280, 1234, 856, 771.

The compounds shown in Table I and II were prepared by the same procedure as described above. The following compounds are also prepared by the same procedure as EXAMPLE 6 and 7.
(4R)-3-[4-(carboxymethyl)benzoyl]-2-(2-hydroxyphenyl)-4-thiazolidinecarboxylic acid
(4R)-3-[(4-carboxyphenyl)acetyl]-2-phenyl-4-thiazolidinecarboxylic acid
(4R)-3-(4-carboxy-3-butenoyl)-2-(2-hydroxyphenyl)-4-thiazolidinecarboxylic acid (4R)-3-(4-carboxy-2-butenoyl)-2-(2-hydroxyphenyl)-4-thiazolidinecarboxylic acid (4R)-3-(4-carboxy-3-butynoyl)-2-(2-hydroxyphenyl)-4-thiazolidinecarboxylic acid

EXAMPLE 8

(4R)-3-[3-(N-Hydroxycarbamoyl)propanoyl]-2-(2-hydroxyphenyl)-4-thiazolidinecarboxylic acid ethyl ester (compound 10a)

To a stirred solution of (4R)-3-(3-carboxypropanoyl)-2-(2-hydroxyphenyl)-4-thiazolidinecarboxylic acid ethyl ester (compound 8a) (1.06 g) and N-methylmorpholine (0.33 ml) in 20 ml of anhydrous tetrahydrofuran, isobutyl chloroformate (0.39 ml) was added dropwise at −15° C., and stirred for additional 2 hours at this temperature. To this solution, the methanol solution of hydroxylamine (0.3 g) was added dropwise at −50° C. The reaction mixture was stirred for 1 hour at room temperature, acidified with N hydrochloric acid, and extracted with ethyl acetate. The organic layer was washed with saturated sodium chloride solution, dried over anhydrous magnesium sulfate, and concentrated in vacuo. The residual oil was purified by silica gel column chlromatography to give 0.7 g (63%) of the titled compound. IR (KBr, cm$^{-1}$) 3220, 1727, 1625, 1595, 1200, 1092, 753. NMR (acetone-d$_6$, δ): 1.24 (3H, t, J=7.5 Hz, CO$_2$CH$_2$CH$_3$), 2.17–3.07 (4H, m, CO$-$(CH$_2$)$_2$CO), 3.30 (1H, AB$_q$(A part), d, J=10.0, 2.0 Hz, C$_5$—H$_A$), 3.47 (1H, AB$_q$(B part), d, J=10.0, 7.0 Hz, C$_5$—H$_B$), 4.14 (2H, q, J=7.5 Hz, CO$_2$CH$_2$), 5.18 (1H, dd, J=2.0, 7.0 Hz, C$_4$—H), 6.40 (1H, S, C$_2$—H), 6.88–7.27 (4H, m, arom. H), 8.60 (2H, br. s, NHOH), 9.77 (1H, br. s, OH)

The compounds shown in Table I were prepared by the same procedure as described above.

EXAMPLE 9

(4R,4′R)-3,3′-(Nonanedioyl)bis[2-(3-nitrophenyl)-4-thiazolidinecarboxylic acid methyl ester] (compound 46)

To a stirred solution of (4R,4′R)-3,3′-(nonanedioyl)-bis[2-(3-nitrophenyl)-4-thiazolidinecarboxylic acid] (compound 47) (3.3 g) in ethyl acetate (50 ml), 2% ether solution of diazomethane was added dropwise until the yellow color of diazomethane was not disappeared, and stirred continuously for 30 minutes. The reaction mixture was concentrated in vacuo to give 3.3 g (96%) of the tilted compound: mp 61°–63° C. (benzene); $[α]_D^{23}$+79.4° (c=1.0, methanol). IR (KBr, cm$^{-1}$): 1740, 1660, 1530, 1350, 1198, 725.

EXAMPLE 10

(4R)-3-[(2-Carboxymethylthio-3-phenyl)propanoyl]-4-thiazolidinecarboxylic acid (compound 75a and 75b)

(4R)-3-[(2-Mercapto-3-phenyl)propanoyl]-4-thiazolidinecarboxylic acid (1.0 g), potassium carbonate (0.7 g), chloroacetic acid (0.2 g) and potassium iodide (0.05 g) were dissolved in water (5 ml), and stirred for 6 hours at room temperature. The reaction mixture was acidified with 5N hydrochloric acid and extracted with ethyl acetate. The organic layer was washed with saturated sodium chloride solution, dried over anhydrous magnesium sulfate and concentrated in vacuo. The tilted compounds (75a and 75b) were separated from the oily residue by silica gel column chromatography.

|       | 75a         | 75b         |
|-------|-------------|-------------|
| yield | 0.4 g (37%) | 0.5 g (47%) |

|                   | 75a                                                                                                                                                                                                        | 75b                                                                                                                                                                                                        |
|-------------------|------------------------------------------------------------------------------------------------------------------------------------------------------------------------------------------------------------|------------------------------------------------------------------------------------------------------------------------------------------------------------------------------------------------------------|
| $[α]_D^{25}$      | −52.2° (c = 1.2, MeOH)                                                                                                                                                                                     | −60.4° (c = 1.0, MeOH)                                                                                                                                                                                     |
| IR (neat, cm$^{-1}$) | 1720, 1620, 1422, 1217, 756                                                                                                                                                                             | 1722, 1620, 1420, 1215, 755                                                                                                                                                                                |
| NMR (CDCl$_3$,δ)  | 2.67–3.63 (6H, m, —S—CH$_2$—CO$_2$H, C$_5$—H, —CH$_2$—Ph), 3.83–4.83 (3H, m, —CO—CH—S—, C$_7$—H), 4.98 (1H, dd, J = 4.5, 6.5Hz, C$_4$—H), 7.22 (5H, s, —C$_6$H$_5$), 9.55 (—CO$_2$H) | 2.70–3.50 (6H, m, —S—CH$_2$—CO$_2$H, C$_5$—H, —CH$_2$—Ph), 4.00–4.67 (3H, m, —CO—CH—S—, C$_7$—H), 5.02 (1H, dd, J = 4.5, 9.5Hz, C$_4$—H), 7.23 (5H, s, —C$_6$H$_5$), 10.00 (—CO$_2$H) |

The compounds shown in Table IV were prepared by the same procedure as described above.

EXAMPLE 11

(4R)-3-[[(Carboxymethylamino)acetyl]-2-(2-hydroxyphenyl)-4-thiazolidinecarboxylic acid (compound 81)

(4R)-3-Chloroacetyl-2-(2-hydroxyphenyl)-4-thiazolidinecarboxylic acid (6 g) was added to a stirred solution of glycine (1.5 g) in N sodium hydroxide (80 ml), and stirred overnight at room temperature. The solution was adjusted to pH 1.5 by 20% hydrochloric acid and washed with ethyl acetate. The aqueous layer was adjusted to pH 3.2, and the separated crystals were collected by filtration to 3.28 g (48.2%) of the titled compound: mp 181°–182° C. (dec.) (water); $[α]_D^{24}$+271.2° (c=0.5, N—NaOH). IR (KBr, cm$^{-1}$): 3400, 3200, 1740, 1672, 1560, 1440, 1380, 1335, 1212, 752, 648, NMR (K$_2$CO$_3$ in D$_2$O, δ): 3.0–4.3 (6H, m, C$_5$—H, COCH$_2$NHCH$_2$CO$_2$H), 6.33 and 6.43 (1H, each s, C$_2$—H), 6.6–7.3 (3H, m, arom. H), 7.82 (1H, br. d, J=8 Hz, arom. H), 9.0–10.3 (2H, br. s, —OH, —CO$_2$H).

The compounds shown in Table V were prepared by the same procedure as described above.

EXAMPLE 12

(2S)-1-[[(2S)-2-Bis(ethoxycarbonylmethyl)amino]-propanoyl]-2-pyrrolidinecarboxylic acid benzyl ester (compound 88)

Ethyl bromoacetate (0.92 g) was added dropwise under ice-cooling to a stirred solution of L-alanyl-L-proline benzyl ester p-toluenesulfonate (2.24 g) and triethylamine (1.53 ml) in dry methylenechloride. After the addition, the reaction mixture was stirred for 2 hours at room temperature, refluxed for another 5 hours, and washed with water and saturated sodium chloride solution. The organic layer was dried over anhydrous magnesium sulfate and concentrated in vacuo. The residual oil was purified by silica gel column chromatography to give 1.02 g (44.8%) of the titled compound: $[α]_D^{24}$−67.9° (c=1.2, MeOH). IR (neat, cm$^{-1}$): 3460, 1742, 1642, 1428, 1180. NMR (CDCl$_3$, δ): 1.23 (6H, t, J=7 Hz, —CO$_2$CH$_2$CH$_3$), 1.25 (3H, d, J = 7.2Hz, CO—CH—N), CH$_3$ 1.67–2.40 (4H, m, C$_3$—H and C$_4$—H), 3.57 (4H, s, —N—CH$_2$CO$_2$Et), 3.50–4.00 (2H, m, C$_5$—H), 4.13 (4H, q, J=7 Hz, —COCH$_2$CH$_3$), 4.10–4.67

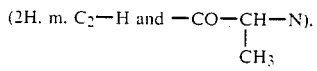
(2H, m, C$_2$—H and —CO—CH—N).

5.03, 5.20 (2H, AB$_q$, J=12 Hz, —CH$_2$—Ph), 7.30 (5H, s, —C$_6$H$_5$).

The compounds shown in Table V were prepared by the same procedure as described above.

EXAMPLE 13

(2S)-1-[[(2S)-Bis(ethoxycarbonylmethyl)amino]-propanoyl]-2-pyrrolidinecarboxylic acid (compound 86)

(2S)-1-[[(2S)-2-bis(ethoxycarbonylmethyl)amino]-propanoyl]-2-pyrrolidinecarboxylic acid benzyl ester (compound 88) (0.50 g) was dissolved in ethanol (10 ml), and hydrogenated with 10% palladium on charcoal catalyst (50 mg). The titled compound was obtained as a colorless oil. Yield 0.40 g (quant. yield); $[\alpha]_D^{24}$ −52.2° (c=1.1, MeOH). IR (neat, cm$^{-1}$): 1742, 1640, 1442, 1190, 1130, 752. NMR (CDCl$_3$, δ): 1.23 (6H, t, J=7 Hz, —CO$_2$CH$_2$CH$_3$), 1.25

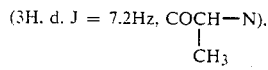
(3H, d, J = 7.2Hz, COCH—N).

1.67–2.50 (4H, m, C$_3$—H and C$_4$—H), 3.53 (4H, s, N—CH$_2$—CO$_2$Et), 3.50–4.00 (2H, m, C$_5$—H), 4.10 (4H, q, J=7 Hz, —CO$_2$CH$_2$CH$_3$), 4.10–4.33

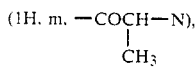
(1H, m, —COCH—N), 4.47 (1H, dd, J=6.5, 5.0 Hz, C$_2$—H), 9.20 (1H, br. s, —CO$_2$H).

The compounds shown in Table V were prepared by the same procedure as described above. The following compounds are also prepared by the same procedure as EXAMPLE 12 and 13.

(2S)-1-[[4-(1-carboxy-3-phenylpropyl)amino]benzoyl]-2-pyrrolidinecarboxylic acid (4R)-3-[[4-(1-carboxy-3-phenylpropyl)amino]benzoyl]-2-(2-hydroxyphenyl)-4-thiazolidinecarboxylic acid

EXAMPLE 14

(2S)-1-[[(2S)-2-(N-Ethoxycarbonylmethyl-N-phenylacetyl)amino]propanoyl]-2-pyrrolidinecarboxylic acid benzyl ester (compound 90)

Phenylacetyl chloride (0.44 ml) was added dropwise at room temperature to a stirred solution of (2S)-1-[[(2S)-2-(ethoxycarbonylmethyl)amino]propanoyl]-2-pyrrolidinecarboxylic acid benzyl ester (1.1 g) and triethylamine (0.47 ml) in dry acetone (15 ml). After the addition, the reaction mixture was stirred for 1 hour at the same temperature, and the precipitate was removed by filtration. The filtrate was evaporated in vacuo, and the residual oil was dissolved in ethyl acetate, and washed with water and saturated sodium chloride solution. The organic layer was dried over anhydrous magnesium sulfate, and evaporated in vacuo. The residual oil was purified by silica gel column chromatography to give 1.3 g (89%) of the titled compound: mp 110°–110.5° C. (benzene-hexane); $[\alpha]_D^{24}$ −114.0° (c=1.0, MeOH). IR (KBr, cm$^{-1}$): 3460, 1739, 1635, 1436, 1200, 1166. NMR (CDCl$_3$, δ): 1.23

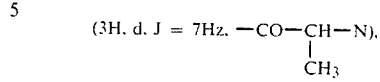
(3H, d, J = 7Hz, —CO—CH—N), 1.28 (3H, t, J=7 Hz, —CO$_2$CH$_2$CH$_3$), 1.67–2.50 (4H, m, C$_3$—H and C$_4$—H), 3.60 (2H, s, —COCH$_2$Ph), 3.33–3.90 (2H, m, C$_5$—H), 4.16 (2H, q, J=7 Hz, —COCH$_2$CH$_3$), 4.23 (2H, s, —N—CH$_2$CO$_2$Et), 4.30–4.60 (1H, m, C$_2$—H), 5.03, 5.23 (2H, AB$_q$, J=12.5 Hz, —CO$_2$CH$_2$Ph), 5.58

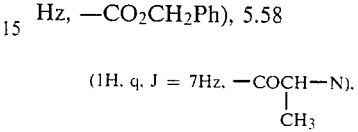
(1H, q, J = 7Hz, —COCH—N).

7.23 (5H, s, —COCH$_2$C$_6$H$_5$), 7.30 (5H, s, —CO$_2$CH$_2$C$_6$H$_5$).

The compounds shown in Table V were prepared by the same procedure as described above.

EXAMPLE 15

(2S)-1-[(2S)-2-[(1-Carboxy-3-phenylpropyl)thio]-propanoyl]-2-pyrrolidinecarboxylic acid (compound 79)

(2S)-1-[(2S)-2-Mercaptopropanoyl]-2-pyrrolidinecarboxylic acid (2.0 g), potassium carbonate (2.8 g) and 2-bromo-4-phenylbutanoic acid (2.9 g) were dissolved in water (40 ml), and stirred overnight at room temperature. The reaction mixture was acidified with 6N hydrochloric acid, and extracted with ethyl acetate. The organic layer was washed with saturated sodium chloride solution, dried over anhydrous magnesium sulfate, and concentrated in vacuo. The residual oil was purified by silica gel column chromatography to give 2.3 g (62%) of the titled compound: $[\alpha]_D^{23}$ −82.2° (c=1.2, MeOH). IR (KBr, cm$^{-1}$): 1740, 1720, 1610, 1455, 1438, 1185, 748, 700.

The compounds shown in Table IV were prepared by the same procedure as described above.

EXAMPLE 16

1-[[(1-Carboxy-3-phenylpropyl)amino]acetyl]-5-(2-hydroxyphenyl)-2-pyrrolidinecarboxylic acid (compound 99)

1-(Chloroacetyl)-5-(2-hydroxyphenyl)-2-pyrrolidinecarboxylic acid [mp 204°–206° C.(dec.), $[\alpha]_D^{24}$ +24.5° (c=1.2, MeOH)] (2.8 g) was added to a stirred solution of 2-amino-4-phenylbutanoic acid (1.8 g) in N sodium hydroxide (40 ml). The reaction mixture was stirred overnight at room temperature. The solution was adjusted to pH 1.5 by 20% hydrochloric acid, and washed with ethyl acetate. The aqueous layer was adjusted to pH 3.0, and the separated solid was collected by filtration to give 1.0 g (24%) of the titled compound. IR (nujol, cm$^{-1}$): 3425, 1735, 1625, 1588.

The compounds shown in Table V were prepared by the same procedure as described above.

In EXAMPLEs and TABLEs I, II, III, IV and V, "a" and "b" of compound No. represent diastereoisomers each other. TABLEs I, II, III, IV and V show various compounds and their physical constants including the compounds specified in EXAMPLEs.

TABLE I

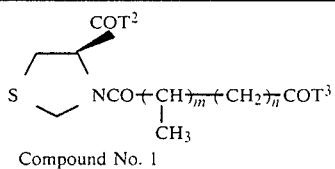

Compound No. 1

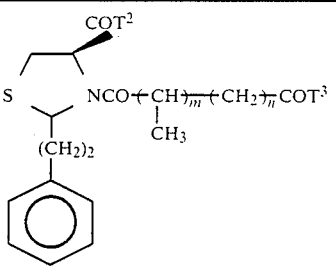

Compound No. 2a and 2b

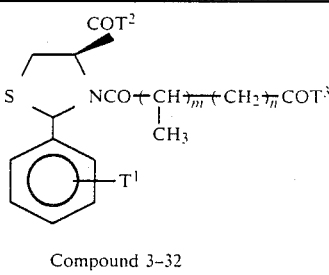

Compound 3-32

| Compd.+ No. | T*1 | T*2 | T*3 | m | n | Method of prepn. (Examp. No.) | Yield (%) | mp (°C.) (Recrystn. solvent) | [α]D deg. (c. solv., °C.) | IR spectrum Sampling*1 method | cm−1 | Rf value*2 (SiO2) |
|---|---|---|---|---|---|---|---|---|---|---|---|---|
| 1 |  | OH | OH | 0 | 6 | 1 | 55 | oil | −84.3 (0.8, MeOH, 26) | C | 1720, 1605, 1420, 1190, 1015, 880 | 0.39 |
| 2a |  | OH | OH | 0 | 3 | 5 | 26 | oil | −19.8 (1.1, MeOH, 24) | C | 1733, 1710, 1650, 1600, 1410, 1240, 1040 | 0.60*3 |
| 2b |  | OH | OH | 0 | 3 | 5 | 51 | oil | −113.8 (1.1, MeOH, 24) | C | 1730, 1650, 1610, 1410, 1240, 1042 | 0.55*3 |
| 3 | 2-OH | OH | OH | 0 | 1 | 1 | 65 | 154.0-154.5 (dec.) (H2O) | +201.4 (0.7, MeOH, 25) | B | 3340, 1725, 1625, 1600, 1460, 1430, 1235, 1100, 915, 770 | 0.25 |
| 4 | 2-OH | OH | OMe | 1 | 1 | 6 | 44 | oil | +161.6 (1.0, MeOH, 25) | A | 3380, 1723, 1624, 1235, 1200, 1174, 764 | 0.51 |
| 5 | 2-OH | OH | OH | 1 | 1 | 7 | 75 | 163-164 (dec.) (EtOAc) | +174.1 (1.0, MeOH, 25) | B | 3330, 1730, 1710, 1629, 1280, 1234, 856, 771 | 0.41 |
| 6 | 2-OH | OH | OH | 0 | 2 | 1 | 75 | 190-191 (dec.) (EtOAc—MeOH) | +181.6 (1.0, MeOH, 27) | B | 3210, 1720, 1618, 1602, 1245, 1173, 940, 763 | 0.35 |
| 7 | 2-OH | OH | OMe | 0 | 2 | 6 | 83 | 165-166 (dec.) (EtOAc) | +164.5 (1.0, MeOH, 25) | A | 3370, 1750, 1693, 1635, 1215, 1165, 755 | 0.47 |
| 8a | 2-OH | OEt | OH | 0 | 2 | 5 | 45 | 181-182 (EtOAc) | −2.8 (0.5, MeOH, 21) | A | 3310, 1727, 1703, 1637, 1595, 1235, 1190, 745 | 0.55 |
| 8b | 2-OH | OEt | OH | 0 | 2 | 5 | 23 | 116-118 (EtOAc) | −311.6 (0.5, MeOH, 21) | A | 3370, 1735, 1708, 1635, 1597, 1220, 1180, 760 | 0.55 |
| 9a | 2-OH | OH | NHOH | 0 | 2 | 7 | 70 | 172-173 (dec.) (EtOH—H2O) |  | A | 3375, 3290, 1720, 1657, 1625, 1590, 1240, 1088, 748 | 0.22 |
| 9b | 2-OH | OH | NHOH | 0 | 2 | 7 | 42 | amorph. |  | A | 3220, 1717, 1655, 1625, 1595, 1225, 1092, 752 | 0.33 |
| 10a | 2-OH | OEt | NHOH | 0 | 2 | 8 | 63 | amorph. |  | A | 3220, 1727, 1625, 1595, 1200, 1092, 753 | 0.25*4 |
| 10b | 2-OH | OEt | NHOH | 0 | 2 | 8 | 31 | amorph. |  |  |  | 0.32*4 |
| 11*5 | 2-OH | OH | OMe | 1 | 2 | 6 | 27 | amorph. | +55.5 (0.8, MeOH, 24) | B | 1738, 1630, 1585, 1310, 1258, 750 |  |
| 11a*5 | 2-OH | OH | OMe | 1 | 2 | 6 | 50 | 205-207 (dec.) (benzene) | +94.6 (0.5, MeOH, 23) | B | 3110, 1730, 1625, 1610, 1192, 1121, 758 |  |
| 12a | 2-OH | OH | OH | 1 | 2 | 7 | 79 | 168-170 (dec.) | +168.0 |  | A | 3370, 1718, | 0.25*4 |

TABLE I-continued

Compound No. 1: structure with S-containing ring, COT² group, NCO(CH)ₘ(CH₂)ₙCOT³, CH₃

Compound No. 2a and 2b: similar structure with (CH₂)₂-phenyl substituent

Compound 3-32: similar structure with phenyl-T¹ substituent

| Compd. No. | T*1 | T*2 | T*3 | m | n | Method of prepn. (Examp. No.) | Yield (%) | mp (°C.) (Recrystn. solvent) | $[\alpha]_D$ deg. (c, solv., °C.) | IR spectrum Sampling*1 method | IR spectrum cm$^{-1}$ | Rf value*2 (SiO$_2$) |
|---|---|---|---|---|---|---|---|---|---|---|---|---|
| 12b | 2-OH | OH | OH | 1 | 2 | 7 | 23 | (acetone-cyclohexane) 163–164 (dec.) (acetone-cyclohexane) | +149.2 (0.4, MeOH, 23) | A | 1625, 1598, 758 3300, 1720, 1708, 1615, 1598, 1242, 753 | 0.25*4 |
| 13 | 2-OH | OH | OH | 0 | 3 | 5 | 65 | 161–162 (dec.) (H$_2$O) | +153.8 (0.5, MeOH, 24) | B | 3190, 1713, 1632, 1598, 1253, 1098, 943, 760 | 0.38 |
| 14 | 2-OH | OH | OEt | 0 | 3 | 6 | 88 | 157–158 (dec.) (EtOAc—benzene) | +145.6 (1.0, MeOH, 25) | A | 3340, 1725, 1638, 1597, 1218, 1120, 768 | 0.48 |
| 15 | H | OH | OH | 0 | 3 | 5 | 73 | 139–140 (EtOAc—MeOH) | +106.3 (1.0, MeOH, 24) | B | 3170, 1753, 1709, 1631, 1423, 1177, 729 | 0.39 |
| 16 | 4-CN | OH | OH | 0 | 3 | 5 | 59 | 190–191 (EtOAc—MeOH) | +137.7 (1.0, MeOH, 24) | B | 2225, 1710, 1665, 1412, 1258 | 0.31 |
| 17 | 2-OH | OH | OH | 0 | 4 | 1 | 62 | amorph. | +115.6 (1.0, MeOH, 24) | B | 3300, 1700, 1622, 1595, 760, 723 | 0.43 |
| 18 | 2-OH | OH | OH | 0 | 5 | 1 | 60 | 158–159 (dec.) (EtOAc) | +128.6 (0.5, MeOH, 25) | B | 3300, 1710, 1620, 1595, 1280, 1095, 895, 850, 760 | 0.47 |
| 19 | H | OH | OH | 0 | 6 | 1 | 33 | oil | +80.5 (1.0, MeOH, 24) |  |  | 0.50 |
| 20 | 2-OH | OH | OH | 0 | 6 | 1 | 61 | 155–157 (dec.) (EtOAc) | +134.1 (0.5, MeOH, 27) | B | 3220, 1710, 1620, 1600, 1415, 1235, 1172, 950, 760 | 0.52 |
| 21 | 2-OH | OH | OH | 0 | 7 | 1 | 63 | 153–154 (dec.) (EtOAc) | +70.9 (0.5, MeOH, 26) | B | 3220, 1705, 1620, 1600, 1415, 1235, 1173, 1090, 830, 760 | 0.55 |
| 22 | 3-NO$_2$ | OH | OH | 0 | 7 | 1 | 45 | oil | +72.1 (0.4, MeOH, 27) | C | 1710, 1615, 1525, 1405, 1350, 1095, 735 | 0.56 |
| 23 | 3-NO$_2$ | OH | OEt | 0 | 7 | 6 | 79 | oil | +72.8 (1.0, MeOH, 23) | C | 1735, 1663, 1620, 1533, 1352, 1240, 1190, 728 | 0.57 |
| 24 | 2-F | OH | OH | 0 | 7 | 1 | 53 | oil | +69.9 (0.5, MeOH, 23) | C | 1730, 1660, 1625, 1587, 1228, 1043, 756 | 0.57 |
| 25 | 3-F | OH | OH | 0 | 7 | 1 | 50 | oil | +63.4 (0.5, MeOH, 23) | C | 1730, 1655, 1610, 1590, 1243, 1042, 775 | 0.57 |
| 26 | 4-F | OH | OH | 0 | 7 | 1 | 48 | oil | +57.9 (0.8, MeOH, 23) |  |  | 0.51*4 |
| 27 | 2-Cl 5-NO$_2$ | OH | OH | 0 | 7 | 1 | 45 | amorph. | +108.3 (0.5, MeOH, 23) | A | 1720, 1660, 1580, 1526, | 0.57 |

TABLE I-continued

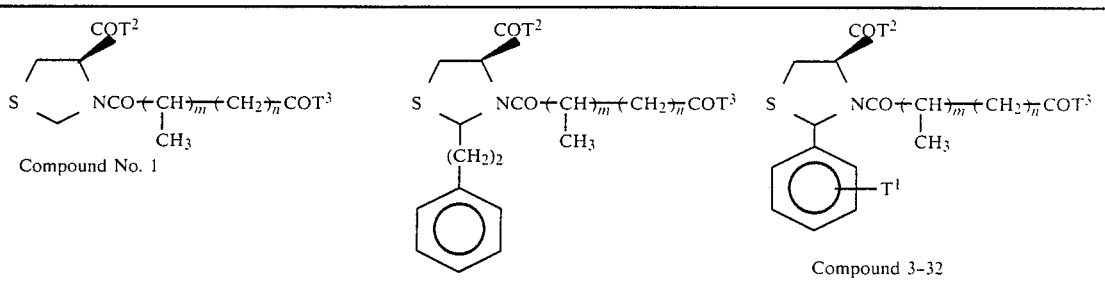

Compound No. 1

Compound No. 2a and 2b

Compound 3-32

| Compd. No. | T*1 | T*2 | T*3 | m | n | Method of prepn. (Examp. No.) | Yield (%) | mp (°C.) (Recrystn. solvent) | [α]_D deg. (c, solv., °C.) | IR spectrum Sampling*1 method | IR spectrum cm$^{-1}$ | Rf value*2 (SiO$_2$) |
|---|---|---|---|---|---|---|---|---|---|---|---|---|
| 28 | 2-OH | OH | OH | 0 | 8 | 1 | 58 | oil | +100.3 (1.0, MeOH, 24) | C | 1240, 1050, 745 1710, 1620, 1600, 1410, 1230, 1090, 850, 760 | 0.58 |
| 29 | 2-OH | OH | OH | 0 | 10 | 1 | 55 | 123–124 (EtOAc—cyclhexane) | +120.4 (0.5, MeOH, 25) | B | 3320, 1705, 1620, 1595, 1410, 1233, 1090, 943, 850, 760 | 0.61 |
| 30 | 3-CN | OH | OH | 0 | 10 | 1 | 56 | oil | +56.4 (0.3, MeOH, 23) | | | 0.56*4 |
| 31 | 2-OH | OH | OH | 0 | 12 | 1 | 59 | amorph. | +101.4 (1.0, MeOH, 24) | B | 3280, 1700, 1620, 1575, 760, 722 | 0.52 |
| 32 | 3-CN | OH | OH | 0 | 12 | 1 | 43 | oil | +61.7 (0.6, MeOH, 23) | | | 0.53*4 |

+a and b represent diastereoisomers of the compound.
*1A; KBr disk, B; nujol mull, C; neat.
*2EtOAc—CHCl$_3$—AcOH (10:5:3).
*3CHCl$_3$—EtOH—AcOH (10:2:1).
*4EtOAc—CHCl$_3$—AcOH (7:5:1).
*5Dicyclohexylamine salt.

TABLE II

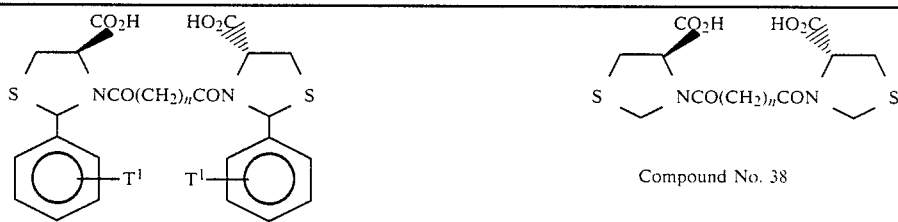

Compound No. 33-37, 39-62

Compound No. 38

| Compd. No. | T$^1$ | n | Method of prepn. (Examp. No.) | Yield (%) | mp (°C.) (Recrystn. solvent) | [α]_D deg. (c, solv., °C.) | IR spectrum Sampling*1 method | IR spectrum cm$^{-1}$ | Rf value*2 (SiO$_2$) |
|---|---|---|---|---|---|---|---|---|---|
| 33 | 2-OH | 4 | 2 | 73 | 124–128 (MeOH) | +182.2 (1.0, DMF, 24) | B | 3280, 1726, 1620, 1596, 775 | 0.23 |
| 34 | 2-OH | 5 | 2 | 67 | oil | +106.1 (0.5, MeOH, 26) | C | 1725, 1625, 1600, 1410, 1235, 1095, 1045, 850, 765 | 0.27 |
| 35 | 3-NO$_2$*5 | 5 | 4 | 69 | 111–113 (dec.) (H$_2$O) | +88.2 (0.5, MeOH, 25) | B | 1635, 1585, 1520, 1355 1095, 730 | 0.28 |
| 36 | 3-CN | 5 | 3 | 59 | 105–112 (H$_2$O) | +115.0 (1.0, MeOH, 25) | B | 2270, 1735, 1640, 1610, 1195, 790 | 0.33 |
| 37 | 4-CN | 5 | 3 | 52 | amorph. | +148.2 (0.9, MeOH, 25) | B | 2255, 1731, 1655, 1620, 785 | 0.32 |
| 38 | | 6 | 2 | 77 | oil | −124.5 (0.5, MeOH, 26) | C | 1720, 1580, 1410, 1180, 1015, 880 | 0.09 |
| 39 | H | 6 | 2 | 79 | amorph. | +97.4 (1.0, MeOH, 24) | B | 1720, 1625, 1585, 732 | 0.42 |
| 40 | 2-OH | 6 | 2 | 86 | amorph. | +123.6 | B | 1720, 1620, 1600, 1230, 1090, | 0.34 |

TABLE II-continued

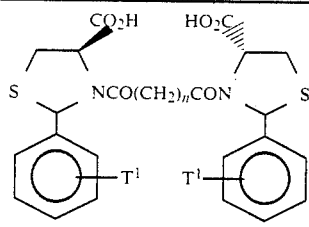

Compound No. 33-37, 39-62

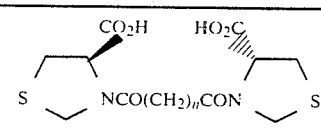

Compound No. 38

| Compd. No. | T[1] | n | Method of prepn. (Examp. No.) | Yield (%) | mp (°C.) (Recrystn. solvent) | [α]$_D$ deg. (c, solv., °C.) | IR spectrum Sampling*[1] method | IR spectrum cm$^{-1}$ | Rf value*[2] (SiO$_2$) |
|---|---|---|---|---|---|---|---|---|---|
| 41 | 3-NO$_2$ | 6 | 2 | 56 | amorph. | +97.5 (0.5, MeOH, 27) | B | 855, 765 1730, 1650, 1605, 1520, 1345, 1095, 730 | 0.34 |
| 42 | 3-CN | 6 | 2 | 58 | amorph. | +98.3 (0.5, MeOH, 21) | B | 2250, 1730, 1640, 1615, 1200, 790 | 0.38 |
| 43 | 4-CN | 6 | 2 | 41 | amorph. | +130.2 (0.9, MeOH, 25) | B | 2248, 1729, 1650, 1618, 790 | 0.36 |
| 44 | 2-OH | 7 | 2 | 75 | amorph. | +142.7 (0.9, MeOH, 25) | B | 1720, 1620, 1600, 1410, 1230, 1173, 1090, 855, 763 | 0.40 |
| 45 | 2-NO$_2$ | 7 | 2 | 47 | amorph. | +191.2 (0.5, MeOH, 26) | B | 1735, 1655, 1515, 1345, 1190, 730 | 0.38 |
| 46*[3] | 3-NO$_2$ | 7 | 9 | 96 | 61-63 (benzene) | +79.4 (1.0, MeOH, 23) | A | 1740, 1660, 1530, 1350, 1198, 725 | 0.57 |
| 47 | 3-NO$_2$ | 7 | 2 | 82 | amorph. | +96.2 (0.5, MeOH, 27) | B | 1725, 1615, 1520, 1445, 1350, 1095, 730 | 0.41 |
| 48 | 4-NO$_2$ | 7 | 2 | 53 | amorph. | +118.5 (0.5, MeOH, 25) | B | 1730, 1650, 1600, 1510, 1345, 1185, 1110, 735 | 0.48 |
| 49 | 3-CN | 7 | 3 | 65 | amorph. | +112.1 (1.1, MeOH, 25) | B | 2250, 1729, 1640, 1610, 790 | 0.41 |
| 50*[5] | 2-F | 7 | 4 | 85 | 140-220 (dec.) (H$_2$O) | +117.5 (1.0, MeOH, 24) | A | 1580, 1225, 1173, 758 | 0.50 |
| 51*[5] | 3-F | 7 | 4 | 88 | 195-210 (dec.) (H$_2$O) | +103.9 (0.50, MeOH, 25) | A | 1590, 1238, 1142, 767 | 0.50 |
| 52 | 4-F | 7 | 2 | 76 | oil | +75.8 (1.0, MeOH, 23) | | | 0.39*[3] |
| 53 | 2-Cl 5-NO$_2$ | 7 | 2 | 79 | amorph. | +167.9 (0.5, MeOH, 23) | A | 1725, 1640, 1575, 1520, 1342, 1047, 740 | 0.51 |
| 54 | 2-OH 5-SO$_2$NH$_2$ | 7 | 2 | 75 | amorph. | +140.9 (0.6, MeOH, 23) | B | 1725, 1620, 1595, 1310, 1150, 930 | 0.42*[4] |
| 55 | 2-OH | 8 | 2 | 68 | amorph. | +122.1 (1.0, MeOH, 24) | B | 3300, 1730, 1628, 1575, 767, 725 | 0.45 |
| 56 | 3-CN | 8 | 2 | 47 | amorph. | +104.6 (1.0, MeOH, 25) | B | 2245, 1726, 1630, 1610, 790 | 0.37 |
| 57 | 3-NO$_2$ | 8 | 2 | 84 | amorph. | +102.2 (0.5, MeOH, 25) | A | 1735, 1620, 1523, 1190, 728 | 0.47 |
| 58*[5] | 3-NO$_2$ | 8 | 4 | 74 | amorph. | +93.9 (0.5, MeOH, 23) | A | 1597, 1520, 1269, 1096, 723 | |
| 59 | 2-OH | 10 | 2 | 61 | 99-100.5 (dec.) (EtOAc—benzene) | +124.7 (0.5, MeOH, 27) | B | 3300, 1740, 1620, 1600, 1565, 1230, 1160, 1090, 895, 770 | 0.49 |
| 60*[5] | 3-CN | 10 | 4 | 63 | 190-195 (H$_2$O) | +109.3 (0.5, H$_2$O, 23) | B | 3400, 2240, 1640, 1600, 1208, 778, 720 | |
| 61 | 2-OH | 12 | 2 | 66 | amorph. | +69.5 (1.0, MeOH, 24) | B | 3300, 1728, 1630, 1590, 762, 725 | 0.45 |
| 62*[5] | 3-CN | 12 | 4 | 52 | amorph. | +104.2 (0.5, MeOH, 23) | B | 3400, 2225, 1605, 1320, 1207, 775, 720 | 0.46*[3] |

*[1] A: KBr disk. B: nujol mull. C: neat.
*[2] EtOAc—CHCl$_3$—AcOH (10:5:3).
*[3] EtOAc—CHCl$_3$—AcOH (7:5:1).
*[4] CHCl$_3$—MeOH—AcOH (3:1:1).
*[5] Disodium salt.
*[6] Dimethyl ester.

TABLE III

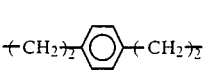

Compound No. 63-68 / Compound No. 69-71

| Compd. No. | T¹ | W | Method of prepn. (Examp. No.) | Yield (%) | mp (°C.) (Recrystn. solvent) | $[\alpha]_D$ deg. (c, solv., °C.) | IR spectrum Sampling*¹ method | cm⁻¹ | Rf value*² (SiO₂) |
|---|---|---|---|---|---|---|---|---|---|
| 63 | 2-OH | —CH₂COCH(COCH₃)— | 5 | 31 | amorph. | +149.2 (1.2, MeOH, 25) | B | 1743, 1720, 1630, 1600, 1238 | 0.38*³ |
| 64 | 2-OH | —CH₂—O—CH₂— | 1 | 35 | amorph. | +138.6 (1.1, MeOH, 25) | A | 3300, 1726, 1640, 1453, 1234, 1142 | 0.24*⁴ |
| 65 | 3-NO₂ | ⟨CH₂⟩₂⟨C₆H₄⟩⟨CH₂⟩₂ | 1 | 36 | amorph. | +81.7 (0.9, MeOH, 24) | A | 3400, 1702, 1618, 1525, 1400, 1347 | 0.55*³ |
| 66 | 2-OH | ⟨CH₂⟩₂O⟨CH₂⟩₂ | 1 | 33 | 136-137 (EtOAc) | +147.6 (0.5, MeOH, 25) | B | 3320, 1750, 1710, 1625, 1595, 1235, 1110, 855, 770 | 0.28 |
| 67 | 2-OH | ⟨CH₂⟩₂S⟨CH₂⟩₂ | 1 | 40 | 159-160 (dec.) (EtOAc) | +136.4 (0.5, MeOH, 27) | B | 3360, 1710, 1627, 1599, 1435, 1235, 1099, 852, 763 | 0.42 |
| 68 | 2-OH | ⟨CH₂⟩₂S⟨CH₂⟩₂S⟨CH₂⟩₂ | 1 | 35 | amorph. | +78.1 (1.0, MeOH, 24) | B | 3300, 1715, 1627, 1590, 760 | 0.31 |
| 69 | 3-NO₂ | ⟨CH₂⟩₂⟨C₆H₄⟩⟨CH₂⟩₂ | 2 | 44 | amorph. | +106.9 (1.1, MeOH, 24) | A | 3425, 1730, 1640, 1525, 1400, 1350 | 0.38*³ |
| 70 | 2-OH | ⟨CH₂⟩₂O⟨CH₂⟩₂ | 2 | 47 | amorph. | +83.0 (0.5, MeOH, 26) | B | 1720, 1625, 1600, 1230, 1090, 850, 760 | 0.15 |
| 71 | 2-OH | ⟨CH₂⟩₂S⟨CH₂⟩₂ | 2 | 53 | amorph. | +129.3 (0.5, MeOH, 27) | B | 1720, 1620, 1600, 1420, 1230, 1093, 852, 763 | 0.30 |

*¹ A: KBr disk, B: nujol mull.
*² EtOAc—CHCl₃—AcOH (10:5:3).
*³ EtOAc—EtOH—AcOH (40:1:1).
*⁴ CHCl₃—EtOH—AcOH (10:2:1).

TABLE IV

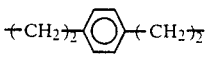

Compound No. 72-76 / Compound No. 77-80

| Compd. No. | T⁴ | T⁵ | T⁶ | T⁷ | Method of prepn. (Examp. No.) | Yield (%) | mp (°C.) (Recrystn. solvent) | $[\alpha]_D$ deg. (c, solv., °C.) | IR spectrum Sampling*¹ method | cm⁻¹ | Rf value*² (SiO₂) |
|---|---|---|---|---|---|---|---|---|---|---|---|
| 72a | H | CH₃ | Ph | H | 10 | 38 | 151-153 (EtOAc) | −8.6 (1.0, MeOH, 23) | A | 3030, 1737, 1720, 1615, 1413, 1215, 1150, 717 | 0.26*³ |

TABLE IV-continued

Compound No. 72-76        Compound No. 77-80

| Compd. No. | $T^4$ | $T^5$ | $T^6$ | $T^7$ | Method of prepn. (Examp. No.) | Yield (%) | mp (°C.) (Recrystn. solvent) | $[\alpha]_D$ deg. (c, solv., °C.) | IR spectrum Sampling*[1] method | cm$^{-1}$ | Rf value*[2] (SiO$_2$) |
|---|---|---|---|---|---|---|---|---|---|---|---|
| 72b | H | CH$_3$ | Ph | H | 10 | 49 | oil | −161.5 (1.0, MeOH, 23) | C | 1735, 1623, 1413, 1243, 1170, 1043, 699 | 0.22*[3] |
| 73 | ⟨2-hydroxyphenyl⟩ | H | CH$_2$CH$_2$Ph | H | 10 | 81 | amorph. | +122.1 (1.2, MeOH, 25) | A | 1720–1710, 1625, 1600, 1400, 1235, 752, 698 | 0.74 |
| 74 | H | CH$_3$ | CH$_2$CH$_2$Ph | H | 10 | 52 | amorph. | −97.9 (1.1, MeOH, 25) | A | 1720, 1620, 1415, 750, 700 | 0.65 |
| 75a | H | CH$_2$Ph | H | H | 10 | 37 | oil | −52.2 (1.2, MeOH, 25) | C | 1720, 1620, 1422, 1217, 756 | 0.13*[4] |
| 75b | H | CH$_2$Ph | H | H | 10 | 46 | oil | −60.4 (1.0, MeOH, 25) | C | 1722, 1620, 1420, 1215, 755 | 0.13*[4] |
| 76 | H | CH$_2$CH$_2$Ph | H | H | 10 | 84 | oil | −61.2 (1.3, MeOH, 24) | C | 1735, 1630, 1615, 1420, 1242, 1172, 1043, 702 | 0.66 |
| 77 | H | COPh | Et | | 15 | 36 | oil | −46.2 (0.8, MeOH, 30) | C | 1733, 1678, 1632, 1610, 1447, 1258, 1187, 1025, 1001, 751 | 0.32*[3] |
| 78 | H | CH$_2$CH$_2$Ph | H | | 15 | 46 | oil | −48.4 (1.1, MeOH, 26) | C | 1730, 1610, 1450, 1240, 1190, 750, 703 | 0.72*[5] |
| 79 | CH$_3$ | CH$_2$CH$_2$Ph | H | | 15 | 62 | amorph. | −82.2 (1.2, MeOH, 23) | A | 1740, 1720, 1610, 1455, 1438, 1185, 748, 700 | 0.38 |
| 80 | H | COCH$_3$ | Et | | 15 | 45 | oil | −49.6 (0.9, MeOH, 30) | C | 1736, 1597, 1398, 1378, 1333, 1250, 1191, 1047, 860, 752 | 0.29*[3] |

*a and b represent diastereoisomers of the compound.
*[1] A: KBr disk. C: neat.
*[2] EtOAc—CHCl$_3$—AcOH (10:5:3).
*[3] Benzene—EtOAc—EtOH—AcOH (14:14:2:1).
*[4] Benzene—EtOAc—AcOH (25:25:1).
*[5] CHCl$_3$—EtOH—AcOH (10:2:1)

TABLE V

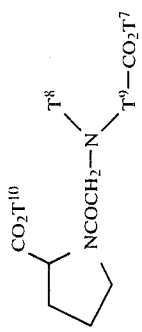

Compound No. 81-85

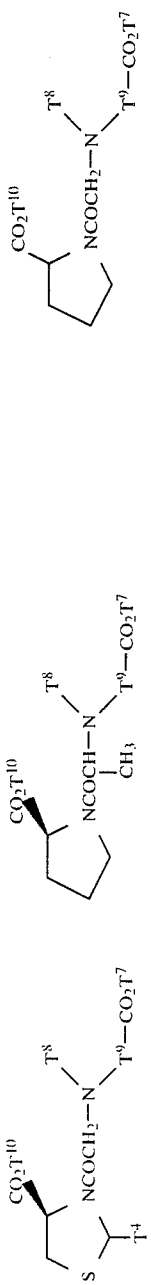

Compound No. 86-98, 100-102

Compound No. 99

| Compd. No. | T⁴ | T⁷ | T⁸ | T⁹ | T¹⁰ | Method of prepn. (Examp. No.) | Yield (%) | mp (°C.) (Recrystn. solvent) | [α]D deg. (c, solv., °C.) | Sampling*¹ method | IR spectrum cm⁻¹ | Rf value (SiO₂) |
|---|---|---|---|---|---|---|---|---|---|---|---|---|
| 81 | 2-OH-phenyl | H | H | —CH₂— | H | 11 | 48.2 | 181-182 (dec.) (H₂O) | +271.2 (0.5, N NaOH, 24) | A | 3400, 3200, 1740, 1672, 1560, 1440, 1380, 1335, 1210, 752 | 0.25*² |
| 82 | phenyl | H | H | —CH₂— | H | 11 | 32.8 | 150-155 (H₂O) | +94.7 (0.5, N NaOH, 23) | B | 3420, 3210, 1650, 1240, 839, 790 | 0.45*³ |
| 83 | 2-OH-phenyl | H | H | 4-methylphenyl | H | 11 | 44.8 | 150-153 (dec.) (EtOH—ether) | +86.5 (0.4, MeOH, 26) | A | 3370–2900, 1655, 1602, 1175 | 0.74*⁴ |
| 84 | 2-OH-phenyl | H | H | 2-methylphenyl | H | 11 | 50.3 | 172-173 (dec.) (EtOAc) | +78.9 (0.8, MeOH, 25) | A | 3350, 1720, 1670, 1644, 1236, 744 | 0.69*⁴ |
| 85 | 2-OH-phenyl | H | H | CH₂CH₂Ph, —CH— | H | 11 | 27.2 | 174-175 (dec.) (H₂O) |  | A | 3400, 1720, 1660, 1610, 1492, 1452, 1240, 752, 700 |  |
| 86 |  | Et | CH₂CO₂Et | —CH₂— | H | 13 | quant. | oil | −52.2 (1.1, MeOH, 24) | C | 1742, 1640, 1442, 1190, 1130, 752 | 0.21*⁵ |
| 87 |  | H | CH₂CO₂H | —CH₂— | H | 7 | 26 | amorph. | −32.8 (1.0, MeOH, 24) | B | 3400, 1720, 1640, 1460, 1380 | 0.10*² |
| 88 |  | Et | CH₂CO₂Et | —CH₂— | CH₂Ph | 12 | 45.2 | oil | −67.9 (1.2, MeOH, 24) | C | 3460, 1742, 1642, 1428, 1180 | 0.70*⁵ |
| 89a |  | H | H | 2-methylphenyl | H | 16 | 33 | 216-218 (dec.) (H₂O) | −141.1 (0.3, MeOH, 23) | B | 2600, 1743, 1550, 1250, 1230, 800 | 0.20*⁶ |

TABLE V-continued

Compound No. 81-85: structure with S, T⁴, CO₂T¹⁰, NCOCH₂—N(T⁸)—T⁹—CO₂T⁷

Compound No. 86-98, 100-102: structure with CO₂T¹⁰, NCOCH—N(T⁸)—T⁹—CO₂T⁷, CH₃

Compound No. 99: structure with CO₂T¹⁰, NCOCH₂—N(T⁸)—T⁹—CO₂T⁷

| Compd. No. | T⁴ | T⁷ | T⁸ | T⁹ | T¹⁰ | Method of prepn. (Examp. No.) | Yield (%) | mp (°C.) (Recrystn. solvent) | $[\alpha]_D$ deg. (c, solv., °C.) | Sampling method*¹ | IR spectrum cm⁻¹ | Rf value (SiO₂) |
|---|---|---|---|---|---|---|---|---|---|---|---|---|
| 89b | (o-tolyl) | H | H | —CH₂— | H | 16 | 45 | 218-226 (dec.) (H₂O) | +1.5 (0.5, MeOH, 23) | B | 3310, 1610, 1575, 1160, 742 | 0.20*⁶ |
| 90 | | Et | COCH₂Ph | —CH₂— | CH₂Ph | 14 | 89 | 110-110.5 (benzene-n-hexane) | −114.0 (1.0, MeOH, 24) | A | 3460, 1739, 1635, 1436, 1200, 1166 | 0.45*⁷ |
| 91 | | Et | COCH₂Ph | —CH₂— | H | 13 | quant. | oil | −99.7 (1.1, MeOH, 23) | D | 1743, 1640, 1445, 1187 | 0.35*⁵ |
| 92 | | H | COCH₂Ph | —CH₂— | H | 7 | 83 | 205-206 (EtOAc—MeOH) | −123.5 | A | 3430, 1727, 1635, 1598, 1426, 1184 | 0.38*⁸ |
| 93 | | Et | CO(CH₂)₂Ph | —CH₂— | CH₂Ph | 14 | 93 | oil | −93.2 (1.0, MeOH, 24) | C | 1746, 1655, 1647, 1447, 1188 | 0.51*⁷ |
| 94 | | Et | CO(CH₂)₂Ph | —CH₂— | H | 13 | quant. | oil | −94.7 | D | 1746, 1642, 1449, 1190 | 0.38*⁵ |
| 95 | | H | CO(CH₂)₂Ph | —CH₂— | H | 7 | 96 | amorph. | −104.3 (1.0, MeOH, 23) | A | 3440, 1735, 1610, 1450, 1185 | 0.45*⁸ |
| 96 | | Et | CH₂Ph | —CH₂— | CH₂Ph | 12 | 46 | oil | −66.0 (1.2, MeOH, 24) | D | 1740, 1639, 1450, 1425, 1185 | 0.57*⁷ |
| 97 | | H | CH₂Ph | —CH₂— | H | 7 | 87 | oil | −59.0 (1.1, MeOH, 25) | A | 3420, 1720, 1638, 1448, 1385 | 0.17*² |
| 98 | | H | COCH₃ | CH₂CH₂Ph —CH— | H | 14 | 62 | 195-196 (dec.) (EtOAc) | | B | 1758, 1720, 1615, 1600, 1380, 750, 700 | 0.66*² |
| 99*¹¹ | (2-hydroxyphenyl) | H | H | CH₂CH₂Ph —CH— | H | 16 | 24 | amorph. | | B | 3425, 1735, 1625, 1588 | |
| 100 | | Et | (piperazine N—CH₂—) | | CH₂Ph | 16 | 37 | oil | −46.9 (0.5, MeOH, 23) | C | 1740, 1642, 1453, 1425, 1170, 740 | 0.20*⁹ |

TABLE V-continued

Compound No. 81-85:
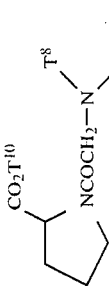

Compound No. 86-98, 100-102:
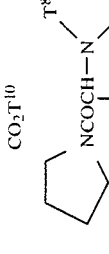

Compound No. 99:
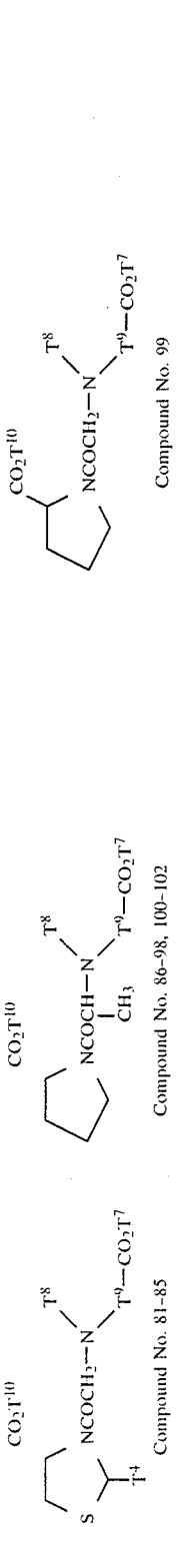

| Compd. No. | T⁴ | T⁷ | T⁸ | T⁹ | T¹⁰ | Method of prepn. (Examp. No.) | Yield (%) | mp (°C.) (Recrystn. solvent) | $[\alpha]_D$ deg. (c, solv., °C.) | IR spectrum Sampling method[*1] cm$^{-1}$ | Rf value (SiO₂) |
|---|---|---|---|---|---|---|---|---|---|---|---|
| 101 | | Et | | $-N\overset{R^8}{\underset{R^9}{\diagdown}} \equiv -N\diagdown N-CH_2-$ | H | 13 | 90 | oil | −35.9 (0.5, MeOH, 23) | | 0.25[*2] |
| 102 | | H | | $-N\overset{R^8}{\underset{R^9}{\diagdown}} \equiv -N\diagdown N-CH_2-$ | H | 7 | 90 | 228–230 (dec.) (0.4, MeOH, 23) | B | 3450, 1720,34[*10] 1610, 1305, 1228, 1200, 680 | |

[a] a and b represent diastereoisomers of the compound.
[*1] A: KBr disk, B: nujol mull, C: Neat, D: liquid cell (CHCl₃).
[*2] n-BuOH—AcOH—H₂O (4:2:1).
[*3] n-BuOH—AcOH—H₂O (4:1:2).
[*4] EtOAc—CHCl₃—AcOH (10:5:3).
[*5] EtOAc—EtOH—AcOH (40:1:1).
[*6] EtOAc—CHCl₃—AcOH (7:5:1).
[*7] Benzene-EtOAc—AcOH (25:25:1).
[*8] CHCl₃—EtOH—AcOH (10:2:1).
[*9] EtOAc
[*10] n-Propanol-28% aq. NH₃ (7:3).
[*11] Starting material: 1-(chloroacetyl)-5-(2-hydroxyphenyl)-2-pyrrolidinecarboxylic acid; mp 204–206° C. (dec.), $[\alpha]_D^{24}$ +24.5° (c = 1.2, MeOH), IR (nujol, cm$^{-1}$) 3370, 1698, 1645, 1610, 1595, 1238, 758.

PHARMACOLOGICAL TEST 1

It has been known that aldose reductase participates in diabetic cataract which is one of the diabetic complications and that appearance is retarded or depressed by inhibition of the aldose reductase [Acta Societatis Ophthalmologicae Japonicae, 80, 1362 (1976)]. The following method is used for the present test.

(Method)

Aldose reductase is purified from rat lenses according to the method of Hoyman et al. [J. Biol. Chem., 240, 877 (1965)]. Action of the compounds (I) of this invention is evaluated by measurement of optical density according to the J. H. Kinoshita's method [Invest. Ophthal., 13, 713 (1974)]. The reaction mixture for the measurement of the aldose reductase activity is 3.0 ml [0.007M phosphate buffer solution (pH 6.2), 0.46M lithium sulfate, $5 \times 10^{-5}$M NADPH, $4 \times 10^{-4}$M DL-glyceraldehyde, 10U aldose reductase, $10^{-4}$ to $10^{-10}$M the compounds (I)] as total volume, and the absorbance thereof is measured at 340 nm.

(Result)

Table VI shows that the compounds (I) of this invention have a strong aldose reductase inhibition effect.

TABLE VI

Inhibitory Activity of the Thiazolidine Compounds against Aldose Reductase

| Compd. No. | $IC_{50}(M)$*[1] |
|---|---|
| 22 | $8.2 \times 10^{-10}$ |
| 23 | $1.1 \times 10^{-8}$ |
| 47 | $1.6 \times 10^{-10}$ |
| 56 | $1.7 \times 10^{-9}$ |
| 57 | $5.4 \times 10^{-9}$ |
| Control*[2] | $1.0 \times 10^{-7}$ |

*[1]Molar concentration of a compound producing 50% inhibition of aldose reductase.
*[2]Quercitrin: referred to Acta Societatis Ophthalmologicae Japonicae, 80, 1369-1370 (1976).

PHARMACOLOGICAL TEST 2

As the method of measurement of angiotensin I-converting enzyme activity, bioassay for the contractile response of isolated smooth muscle or the pressor response of normal animals and biochemical assay for the enzyme isolated from lung or other organs of animals are known. The former is found more advantageous than the latter for the examination of the convertion of angiotensin I to angiotensin II in vivo.

In the present study, therefore, we adopted the bioassay for contractile response of isolated guinea pig ileum to angiotensin I.

(Method)

Isolated guinea pig ileum was suspended in the organ bath containing 20 ml of Tyrode's solution of 30° C. gassed with 95% $O_2$+5% $CO_2$. The contraction induced by the addition of angiotensin I (0.1 μg/ml) at intervals of 10 minutes was recorded on a recticorder (Nihon Koden) for 90 seconds using FD pick up (ST-1T-H, Nihon Koden).

The test compounds were added to the bath 5 minutes before the addition of angiotensin I.

The inhibitory activity of angiotensin I-converting enzyme was calculated by the following formula.

$[(A-B)/A] \times 100$

A: contractile intensity of angiotensin I before addition of the compound
B: contractile intensity of angiotensin I after addition of the compound From the fact that kininase II, which destroys bradykinin having contractive action on isolated guinea pig ileum, is thought to be identical with angiotensin I-converting enzyme, augmentation of the contractile response to bradykinin by test compounds was examined by using bradykinin (0.005 μg/ml) in place of angiotensin I according to the above mentioned method.

(Result)

Concentration of a number of the compounds of this invention, which produced 50% inhibition of angiotensin I activity or augmentation of bradykinin activity inducing the contraction of guinea pig ileum, fell in the range of $10^{-7} \sim 10^{-9}$M.

PHARMACOLOGICAL TEST 3

The activity of angiotensin I-converting enzyme was measured by spectrophotometry according to the method of D. W. Cushman and H. S. Cheung [Biochem. Pharmacol., 20, 1637 (1971)]. That is, the absorbance of hippuric acid was measured, which is liberated by incubating hippuryl-L-histidyl-L-leucine (HHL) as substrate in the presence of angiotensin I-converting enzyme extracted from rabbit lung.

(Method)

The reaction mixture is as follows:
100 mM phosphate buffer (pH 8.3)
300 mM sodium chloride
5 mM HHL
$10^{-3} \sim 10^{-9}$M enzyme inhibitor
5 mU enzyme 0.25 ml of the above mixture was incubated at 37° C. for 30 minutes and the reaction was stopped by adding 0.25 ml of 1N hydrochloric acid. To this solution, 1.5 ml of ethyl acetate was added in order to extract hippuric acid. 1.0 ml of ethyl acetate layer was collected and evaporated to dryness, and the residue obtained was dissolved in 1.0 ml of water. The absorbance of this solution was measured at 228 nm.

The inhibitory activity of angiotensin I-converting enzyme was calculated by the following formula:
Percent inhibition = $[(A-B)/A] \times 100$ A: absorbance of reaction solution before addition of the compound
B: absorbance of reaction solution after addition of the compound Concentration of compound producing 50% inhibition of angiotensin I-converting enzyme ($IC_{50}$)

The solution containing compounds at the concentration of $1 \times 10^{-3}$M to $1 \times 10^{-9}$M was incubated and percent inhibition at each concentration was calculated according to the above formula, and then $IC_{50}$, concentration of the compound producing 50% inhibition of the enzyme activity, was determined.

(Result)

$IC_{50}$ of a number of the compounds of this invention, fell in the range of $10^{-7} \sim 10^{-10}$M.

TOXICITY TEST

The acute toxicity of compounds 47 and 56 is 1000~1500 mg/kg.

(Experimental animals)

The male ddy-std. strain mice (4 weeks of age, weighing 19-21 g) were placed in a breeding room of constant temperature and humidity (23±1° C., 55±5%) and fed freely pellet diet (CE-2, Clea Japan, Inc.) and water ad libitum for a week. The mice showing the normal growth were selected for the experiment.

(Method of administration)

Test compounds are dissolved in distilled water and administered (i.v.) in a dose of 0.5 ml/20 g body weight.

It is found in the above pharmacological and toxicity test that the compounds (I) of this invention are useful as drugs for therapy or prophylaxis of the diabetic complications and as antihypertensive agents.

In case the compounds are used for preventing or relieving diabetic complications, the dosage forms are tablet, capsule, granule, powder, suppository, injection, ophthalmic solution, ophthalmic ointment, etc. These preparations can also contain general excipients.

On the other hand, in case the compounds are used for reducing blood pressure, they can be given with the combination of diuretics such as probenecid, carinamide, hydroflumethiazide, furosemide, and bumetanide same as other antihypertensive agents. The compounds can be administered either orally or parenterally. The dosage forms are tablet, capsule, granule, powder, suppository, injection, etc. In the treatment of hypertension, these preparations can contain not only general excipients but also other antihypertensive agents such as reserpine, α-methyldopa, guanethidine, clonidine, hydralazine, etc., or β-adrenergic blocking agents such as propranolol, alprenolol, pindolol, bufetolol, bupranolol, bunitrolol, practolol, oxprenolol, indenolol, timolol, bunolol, etc.

The dose is adjusted depending on symptom, dosage form, etc. But, usual daily dosage is 1 to 5000 mg, preferably 10 to 1000 mg, in one or a few divided doses.

EXAMPLES OF FORMULATION (1) Oral drug (a) tablet

| | |
|---|---|
| compound 13 | 50 mg |
| lactose | 120 mg |
| crystalline cellulose | 60 mg |
| calcium carboxymethylcellulose | 7 mg |
| magnesium stearate | 3 mg |
| Total | 240 mg |
| compound 22 | 100 mg |
| lactose | 95 mg |
| crystalline cellulose | 45 mg |
| calcium carboxymethylcellulose | 7 mg |
| magnesium stearate | 3 mg |
| Total | 240 mg |
| compound 23 | 150 mg |
| lactose | 60 mg |
| crystalline cellulose | 30 mg |
| calcium carboxymethylcellulose | 7 mg |
| magnesium stearate | 3 mg |
| Total | 250 mg |
| compound 56 | 150 mg |
| lactose | 60 mg |
| crystalline cellulose | 30 mg |
| calcium carboxymethylcellulose | 7 mg |
| magnesium stearate | 3 mg |
| Total | 250 mg |
| compound 74 | 150 mg |
| lactose | 60 mg |
| crystalline cellulose | 30 mg |
| calcium carboxymethylcellulose | 7 mg |
| magnesium stearate | 3 mg |
| Total | 250 mg |
| compound 88 | 150 mg |
| lactose | 60 mg |
| crystalline cellulose | 30 mg |
| calcium carboxymethylcellulose | 7 mg |
| magnesium stearate | 3 mg |
| Total | 250 mg |

The tablets may be treated with common film-coating and further with sugar-coating.

(b) granule

| | |
|---|---|
| compound 13 | 30 mg |
| polyvinylpyrrolidone | 25 mg |
| lactose | 385 mg |
| hydroxypropylcellulose | 50 mg |
| talc | 10 mg |
| Total | 500 mg |
| compound 22 | 30 mg |
| polyvinylpyrrolidone | 25 mg |
| lactose | 385 mg |
| hydroxypropylcellulose | 50 mg |
| talc | 10 mg |
| Total | 500 mg |
| compound 94 | 30 mg |
| polyvinylpyrrolidone | 25 mg |
| lactose | 385 mg |
| hydroxypropylcellulose | 50 mg |
| talc | 10 mg |
| Total | 500 mg |

(c) powder

| | |
|---|---|
| compound 13 | 250 mg |
| lactose | 240 mg |
| starch | 480 mg |
| colloidal silica | 30 mg |
| Total | 1000 mg |
| compound 65 | 300 mg |
| lactose | 230 mg |
| starch | 440 mg |
| colloidal silica | 30 mg |
| Total | 1000 mg |
| compound 79 | 300 mg |
| lactose | 230 mg |
| starch | 440 mg |
| colloidal silica | 30 mg |
| Total | 1000 mg |
| compound 100 | 300 mg |
| lactose | 230 mg |
| starch | 440 mg |
| colloidal silica | 30 mg |
| Total | 1000 mg |

(d) capsule

| | |
|---|---|
| compound 13 | 50 mg |
| lactose | 102 mg |
| crystalline cellulose | 36 mg |
| colloidal silica | 2 mg |
| Total | 190 mg |
| compound 23 | 100 mg |
| lactose | 52 mg |
| crystalline cellulose | 36 mg |
| colloidal silica | 2 mg |
| Total | 190 mg |
| compound 74 | 200 mg |
| glycerin | 179.98 mg |
| butyl p-hydroxybenzoate | 0.02 mg |
| Total | 380 mg |
| compound 81 | 30 mg |
| glycerin | 349.98 mg |
| butyl p-hydroxybenzoate | 0.02 mg |
| Total | 380 mg |
| compound 98 | 200 mg |
| glycerin | 179.98 mg |
| butyl p-hydroxybenzoate | 0.02 mg |

-continued
EXAMPLES OF FORMULATION
(1) Oral drug

| | |
|---|---|
| Total | 380 mg |

(2) Injection (a) 1 to 30 mg of compound 9B is contained in 1 ml of the aqueous solution (pH 6.5–7.0).
(b) 1 to 30 mg of compound 73 is contained in 1 ml of the aqueous solution (pH 6.5–7.0).

(3) Ophthalmic solution

The following composition is contained in 5 ml of the aqueous solution (pH 6.0).
Compound 23—50 mg
propyl p-hydroxybenzoate—0.7 mg
methyl p-hydroxybenzoate—1.3 mg
sodium hydroxide—proper quantity (4) Ophthalmic ointment The following composition is contained in 1 g.
compound 22—20 mg
white petrolatum—889.8 mg
mineral oil—100 mg
butyl p-hydroxybenzoate—0.2 mg (5) Suppository The following composition is contained in 1 g.
compound 47—50 mg
polyethylene glycol 1000—800 mg
polyethylene glycol 4000—150 mg

We claim:

1. A compound of formula (I)

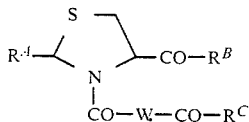  (I)

wherein
$R^A$ is selected from the group consisting of
(a) phenyl and naphthyl;
(b) phenyl substituted by at least one substituent selected from the group consisting of lower alkyl, hydroxy, lower alkoxy, halogenolower alkoxy, acetoxy, halogen, nitro, cyano, carboxy, sulfamoyl and lower alkylsulfinyl;
$R^B$ is hydroxy or lower alkoxy;
$R^C$ is hydroxy, lower alkoxy or

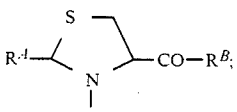

W is selected from the group consisting of

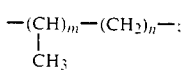 (a)

$-(CH_2)_p-X-(CH_2)_q-$; and (b)

$-(CH_2)_p-Y-(CH_2)_r-Y-(CH_2)_t-$. (c)

wherein
m is 0 or 1;
n is from 1 to 12;
p, r and t are each 1, 2 or 3;
q is 2 or 3;
X is O, SO or $SO_2$; and
Y is O, S, SO or $SO_2$,
and salts thereof, said lower alkyl, lower alkanoyl and lower alkoxy having 1 to 6 carbon atoms.

2. The compound of claim 1 wherein W is $-(CH_2)_2-O-(CH_2)_2-$.

3. The compound of claim 1 wherein $R^A$ is selected from phenyl, 4-fluorophenyl, 2-nitrophenyl, 3-nitrophenyl, 4-nitrophenyl, 2-hydroxyphenyl, 3-cyanophenyl 4-cyanophenyl, and 2-hydroxy-5-sulfamoylphenyl.

4. The compound of claim 1 which is (4R)-3-[8-(ethoxycarbonyl)octanoyl]-2-(3-nitrophenyl)-4-thiazolidinecarboxylic acid.

5. The compound of claim 1 which is (4R,4′R)-3,3′-(nonanedioyl)bis[2-(3-nitrophenyl)-4-thiazolidinecarboxylic acid methyl ester].

6. The compound of claim 1 which is (4R)-3-(11-carboxyundecanoyl)-2-(3-cyanophenyl)-4-thiazolidinecarboxylic acid.

7. The compound of claim 1 which is (4R,4′R)-3,3′-(decanedioyl)bis[2-(3-cyanophenyl)-4-thiazolidinecarboxylic acid].

8. The compound of claim 1 which is (4R,4′R)-3,3′-(dodecanedioyl)bis[2-(3-cyanophenyl)-4-thiazolidinecarboxylic acid].

9. The compound of claim 1 which is (4R)-3-(8-carboxyoctanoyl)-2-(3-nitrophenyl)-4-thiazolidinecarboxylic acid.

10. The compound of claim 1 which is (4R,4′R)-3,3′-(nonanedioyl)bis[2-(3-nitrophenyl)-4-thiazolidinecarboxylic acid].

11. The compound of claim 1 which is (4R)-3-(7-carboxyheptanoyl)-2-(2-hydroxyphenyl)-4-thiazolidinecarboxylic acid.

12. The compound of claim 1 which is (4R)-3-(4-carboxybutanoyl)-2-(2-hydroxyphenyl)-4-thiazolidinecarboxylic acid.

13. The compound of claim 1 wherein W is selected from $-CH(CH_3)-CH_2-$, $-(CH_2)_{1-8}$, $-(CH_2)_{10}-$ and $-(CH_2)_{12}-$.

14. A composition comprising an amount of the compound of claim 1 sufficient to reduce blood pressure and a pharmaceutically acceptable excipient.

15. A method of reducing blood pressure in a warm blooded animal which comprises administering the composition of claim 14 to said warm blooded animal.

16. A composition comprising an amount of the compound of claim 1 sufficient to prevent or relieve diabetes mellitus associated complications consisting of cataracts, neuropathy, nephropathy and retinopathy in a diabetic mammal, and a pharmaceutically acceptable excipient.

17. A method of preventing or relieving diabetes mellitus associated complications consisting of cataracts and retinopathy in a diabetic mammal which comprises administering the composition of claim 16 to said diabetic mammal.

* * * * *

UNITED STATES PATENT AND TRADEMARK OFFICE
CERTIFICATE OF CORRECTION

PATENT NO. : 4,499,102    PAGE 1 OF 7.
DATED      : February 12, 1985
INVENTOR(S): Masayuki OYA et al It is certified that error appears in the above-identified patent and that said Letters Patent is hereby corrected as shown below:

Column 4, line 66, change "metioned" to --mentioned--.

Column 5, line 20, change "structure" to --reactive--.

Column 6, line 30, change "alminum" to --aluminum--.

Column 6, line 59, change "$+CH_2 - CH_2)_4 CH_2-)$" to

-- $-CH_2 +CH_2\underline{)_4} CH_2-)$ --.

Coluumn 6, line 60, change "$-CH_2 +CH_2)_4 CH_2-)$" to

-- $-\underline{CH_2} +CH_2)_{\underline{4}} \underline{CH_2}-)$ --.

Column 8, lines 16-17, change "$-CH_2 -+CH_2)_4 CH_2-)$" to

-- $-CH_2 -+CH_2\underline{)_4} CH_2-)$ --.

Column 8, line 17, change "$-CH_2 -+CH_2)_4 CH_2)$" to

-- $-\underline{CH_2} -+CH_2)_{\underline{4}} \underline{CH_2})$ --.

UNITED STATES PATENT AND TRADEMARK OFFICE
CERTIFICATE OF CORRECTION

PATENT NO. : 4,499,102          PAGE 2 OF 7.

DATED : February 12, 1985

INVENTOR(S) : Masayuki OYA et al

It is certified that error appears in the above-identified patent and that said Letters Patent is hereby corrected as shown below:

Column 8, lines 40-41, change "$-(CH_2-CH_2)_3CH_2-)$" to

-- $-CH_2-(CH_2)_3CH_2-)$ --.

Column 8, line 62, after "thiazolidinecarboxylic" insert

--acid--.

Column 11, line 24, change "chlromatography" to

--chromatography--.

Column 11, line 27, change "$CO-(CH_2)_2CO)$" to

-- $CO-(CH_2)_2CO)$ --.

Column 11, line 47, change "tilted" to --titled--.

Column 11, line 55, change "thizolidinecarboxylic" to

--thiazolidinecarboxylic--.

UNITED STATES PATENT AND TRADEMARK OFFICE
CERTIFICATE OF CORRECTION

PAGE 3 OF 7.

PATENT NO. : 4,499,102
DATED : February 12, 1985
INVENTOR(S) : Masayuki OYA et al It is certified that error appears in the above-identified patent and that said Letters Patent is hereby corrected as shown below:

Column 12, in the Table at the top of the column, in the middle vertical column headed "75a":

line 6, change "$-S-CH_2\ -CO_2H,$" to -- $-S-\underline{CH_2}-CO_2H,$ --.

line 7, change "$-CH_2-Ph),$" to -- $-\underline{CH_2}-Ph),$ --.

line 9, change "$-CO-CH-S-,C_2-H),$" to

-- $-CO-\underset{|}{\underline{CH}}-S-,C_2-H),$ --.

Column 12, in the Table at the top of the column, in the right column headed "75b":

line 6, change "$-S-CH_2-CO_2H,$" to -- $-S-\underline{CH_2}-CO_2H,$ --.

line 7, change "$C_5-H,-CH_2-Ph),$" to -- $-C_5-H,-\underline{CH_2}-Ph),$ --.

UNITED STATES PATENT AND TRADEMARK OFFICE
CERTIFICATE OF CORRECTION

PATENT NO. : 4,499,102
DATED : February 12, 1985
INVENTOR(S) : Masayuki OYA et al It is certified that error appears in the above-identified patent and that said Letters Patent is hereby corrected as shown below:

line 9, change "$-CO-CH-S-,C_2-H)$" to -- $-CO-\underline{CH}-S,C_2-H)$ --.

Column 12, line 65, "$CO-CH-N),$" should read -- $CO-CH-N),$ --.
$\phantom{CO-}|$ $\phantom{CO-CH-N), should read --CO-}|$
$\phantom{CO-}CH_3$ $\phantom{CO-CH-N), should read --CO-}\underline{CH_3}$ Column 13, line 3, change "$-COCH_2CH_3)$" to -- $-CO\underline{CH_2}CH_3)$ --.

Column 13, line 4, change "$-CO-CH-N),$" to -- $-CO-\underline{CH}-N),$ --.
$\phantom{CO-xx}|$ $\phantom{to -- -CO-xx}|$
$\phantom{CO-xx}CH_3$ $\phantom{to -- -CO-xx}CH_3$ Column 13, line 23, change "(quant. yild)" to -- (quant.yield) --.

Column 13, line 36, change "$(1H,m, -COCH-N),$" to
$\phantom{xxxxxxxxxxxxxxxxxxxxxxxxxxx}|$
$\phantom{xxxxxxxxxxxxxxxxxxxxxxxxxxx}CH_3$ -- $(1H,m, -CO\underline{CH}-N),$ --.
$\phantom{xx}|$
$\phantom{xx}CH_3$

UNITED STATES PATENT AND TRADEMARK OFFICE
CERTIFICATE OF CORRECTION

PATENT NO. : 4,499,102          PAGE 5 OF 7.
DATED     : February 12, 1985
INVENTOR(S) : Masayuki OYA et al It is certified that error appears in the above-identified patent and that said Letters Patent is hereby corrected as shown below:

Column 14, line 4, change "-CO-CH-N),"    to -- -CO-CH-N),--.
                            |                      |
                           $CH_3$                 $\underline{CH_3}$ Column 14, line 14, change "-$CO_2CH_2$PH),"  to -- -$CO_2\underline{CH_2}$Ph),--.

Column 14, line 16, change "-CO$\underline{CH}$-N),"  to -- -COC$\underline{H}$-N),--.
                              |                            |
                            $CH_3$                       $CH_3$ Column 15, in the vertical column entitled "Method of prepn. (Examp. No.), on the horizontal line for "Compd. No. 6", below "1" insert --5--.

Column 21, in the vertical column entitled "Compd. No.", on the sixth horizontal line from the top, change "46*$^3$" to --46$^{*6}$ --.

UNITED STATES PATENT AND TRADEMARK OFFICE
CERTIFICATE OF CORRECTION

PATENT NO. : 4,499,102

DATED : February 12, 1985

INVENTOR(S) : Masayuki OYA et al

It is certified that error appears in the above-identified patent and that said Letters Patent is hereby corrected as shown below:

Column 27 and 28, Table V, the upper right-hand structural formula should be:

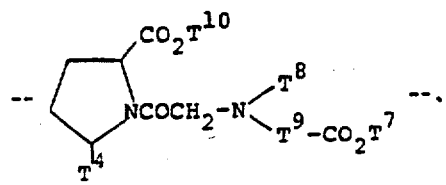

Columns 31 and 32, Table V, "For Compd. No. 102", the information in the five right-hand vertical columns should be:

| | | | | |
|---|---|---|---|---|
| 228-230 (dec.) (MeOH) | -33.9 (0.4, MeOH, 23) | B | 3450, 1720, 1610, 1305, 1228, 1200, 680 | $0.34^{*10}$ |
| -- | | | | --.. |

UNITED STATES PATENT AND TRADEMARK OFFICE
CERTIFICATE OF CORRECTION

PATENT NO. : 4,499,102

DATED : February 12, 1985

INVENTOR(S) : Masayuki OYA et al

It is certified that error appears in the above-identified patent and that said Letters Patent is hereby corrected as shown below:

Column 33, line 50, change "convertion" to --conversion--.

Column 38, line 49, change "-$(CH_2)_{1-8}$," to -- -$(CH_2)_{\overline{1-8}}$, --.

Signed and Sealed this

Twentieth Day of January, 1987

Attest:

DONALD J. QUIGG

Attesting Officer

Commissioner of Patents and Trademarks